(12) United States Patent
Tang et al.

(10) Patent No.: US 9,618,453 B2
(45) Date of Patent: Apr. 11, 2017

(54) AGGREGATION INDUCED EMISSION OF FLUORESCENT BIOPROBES AND METHODS OF USING THE SAME

(71) Applicant: THE HONG KONG UNIVERSITY OF SCIENCE AND TECHNOLOGY, Kowloon, Hong Kong (CN)

(72) Inventors: Benzhong Tang, Hong Kong (CN); Ka Ming Ng, Hong Kong (CN); Qian Luo, Hong Kong (CN); Yong Yu, Hong Kong (CN); Yuning Hong, Hong Kong (CN); Jianzhao Liu, Hong Kong (CN); Sijie Chen, Hong Kong (CN); Wing Yip Lam, Hong Kong (CN); Zhengke Wang, Hong Kong (CN); Wei Qin, Hong Kong (CN); Tsz Kin Kwok, Hong Kong (CN)

(73) Assignee: THE HONG KONG UNIVERSITY OF SCIENCE AND TECHNOLOGY, Kowloon, Hong Kong (CN)

( * ) Notice: Subject to any disclaimer, the term of this patent is extended or adjusted under 35 U.S.C. 154(b) by 116 days.

(21) Appl. No.: 13/899,070

(22) Filed: May 21, 2013

(65) Prior Publication Data
US 2013/0266953 A1   Oct. 10, 2013

Related U.S. Application Data

(63) Continuation-in-part of application No. 13/649,819, filed on Oct. 11, 2012, now Pat. No. 9,409,928.

(60) Provisional application No. 61/627,336, filed on Oct. 11, 2011, provisional application No. 61/688,787, filed on May 22, 2012, provisional application No. 61/688,845, filed on May 23, 2012.

(51) Int. Cl.
| | | |
|---|---|---|
| *C12Q 1/04* | (2006.01) | |
| *G01N 21/64* | (2006.01) | |
| *B82Y 15/00* | (2011.01) | |
| *G01N 1/30* | (2006.01) | |
| *C07F 7/08* | (2006.01) | |

(52) U.S. Cl.
CPC .......... *G01N 21/6486* (2013.01); *B82Y 15/00* (2013.01); *C07F 7/0809* (2013.01); *C07F 7/0816* (2013.01); *G01N 1/30* (2013.01); *G01N 21/6428* (2013.01); *G01N 21/6458* (2013.01); *G01N 2021/6439* (2013.01)

(58) Field of Classification Search
None
See application file for complete search history.

(56) References Cited

U.S. PATENT DOCUMENTS

| | | | |
|---|---|---|---|
| 5,362,628 A | 11/1994 | Haugland et al. | |
| 6,277,643 B1 | 8/2001 | Choi et al. | |
| 7,939,613 B2* | 5/2011 | Tang et al. | 526/329.1 |
| 8,129,111 B2* | 3/2012 | Tang et al. | 435/6.1 |
| 9,409,928 B2* | 8/2016 | Tang | B82Y 15/00 |
| 2008/0220407 A1* | 9/2008 | Tang et al. | 435/4 |
| 2010/0009362 A1* | 1/2010 | Tang et al. | 435/6 |
| 2012/0172296 A1* | 7/2012 | Tang et al. | 514/5.9 |
| 2012/0237964 A1* | 9/2012 | Tang et al. | 435/29 |

OTHER PUBLICATIONS

Liu et al. Chem. Eur. J. (2010) 16: 8433-8438 published online Jun. 11, 2010.*
Lim et al. Chem. Mater. (2009) 21: 5819-5825.*
Tyagarajan et al. Electrophoresis (2003) 24: 2348-22358.*
Nakamura et al. Chem. Eur. J. (2011) 17: 5344-5349 published online Mar. 24, 2011.*
Tong et al. J. Phys. Chem. B (2007) 111: 11817-11823.*
Wu et al. Chem. Soc. Rev. (2011) 40: 3483-3495, published on the Web Mar. 29, 2011.*
Yu et al. Chem. Comm. (2012) 48: 6360-6362, published on the Web May 4, 2012.*
Hong et al. Chemistry: A European Journal (2010) 16: 1232-1245.*
Farrell, E., et al., "Effects of iron oxide incorporation for long term cell tracking on MSC differentiation in vitro and in vivo", Biochemical and Biophysical Research Communications, 369, pp. 1076-1081, (2008).
Cox, W. G., et al. "Fluorescent DNA hybridization probe preparation using amine modification and reactive dye coupling", Bio Techniques, vol. 36, No. 1, pp. 114-122, (2004).

* cited by examiner

*Primary Examiner* — Susan Hanley
(74) *Attorney, Agent, or Firm* — Nath, Goldberg & Meyer; Joshua B. Goldberg

(57) ABSTRACT

Provided herein are fluorescent bioprobes comprising fluorogens that exhibit aggregation-induced emission (AIE) labeled on biomolecules. The present subject matter relates to a fluorescent bioprobe comprising one or more fluorogen labeled on chitosan. The present subject matter is also directed to methods of preparing the fluorescent bioprobes, methods of labeling and detecting DNA and/or proteins with the fluorescent bioprobe, and methods of cell imaging including live cell tracking.

9 Claims, 18 Drawing Sheets
(14 of 18 Drawing Sheet(s) Filed in Color)

AGGREGATION INDUCED EMISSION OF FLUORESCENT BIOPROBES AND METHODS OF USING THE SAME

RELATED APPLICATIONS

The present patent application is a continuation-in-part of prior patent application Ser. No. 13/649,819, filed Oct. 11, 2012, which claims priority to provisional Patent Application No. 61/627,336, filed Oct. 11, 2011, both of which are incorporated by reference herein in their entirety. Furthermore, the present patent application also claims priority to provisional Patent Application No. 61/688,787 and 61/688,845, filed May 22, 2012 and May 23, 2012, respectively, by the inventors hereof and are incorporated by reference herein in their entirety.

The Sequence Listing submitted in text format (.txt) filed on May 21, 2013, named "Sequence_listing_05102013_ST25.txt", (created on May 10, 2013, 6 KB), is incorporated herein by reference.

TECHNICAL FIELD

The present subject matter relates generally to development of fluorescent organic compounds that exhibit aggregation induced emission. The fluorescent fluorogens were synthesized with amine- or thiol-reactive functional groups, or functional groups making them water soluble. The present subject matter also relates to using the fluorescent fluorogens for labeling of biomolecules and cell imaging.

BACKGROUND

Fluorescent probes used to detect important biological events in living cells or animals have been in increasing demand in the biological and biomedical fields over the past two decades. Many kinds of fluorescent bioprobes have been developed, such as organic dyes, inorganic nanoparticles, and fluorescent polymers.

Traditional commercially available organic dyes, such as fluorescein isothiocyanate (FITC), rhodamine, propidium iodide, ethidium bromide, and nile red, are highly emissive in dilute solutions but become weakly fluorescent or even non-emissive in the aggregated state. This problem, termed aggregation-caused quenching (ACQ), has seriously obstructed the advancement of fluorescent sensors. It has been attributed to the nonradiative decay of sandwich-shaped excimers and exciplexes formed among the closely packed dye molecules in the aggregates. A low dye concentration staining the cell may be free of aggregation but can only offer weak emission, and the small number of dye molecules that enter into the cell may be easily photobleached during the imaging process. Therefore, the fluorescence emission can be further weakened, rather than enhanced, if more fluorophores are loaded into the cell due to the ACQ effect. Accordingly, the dyes are usually used in trace amounts (often at nM level).

Such problems can be avoided by the use of inorganic quantum dots (QDs), which are highly fluorescent and resistant to photobleaching. However, QDs need improved hydrophilicity and reduced toxicity, as they are usually composed of heavy metals and chalcogens (e.g. CdS, CdSe, ZnSe, and PdTe), which are well known toxicants or carcinogens.

Another approach to mitigate the ACQ effect of traditional organic dyes is labeling them onto macromolecular chains to form fluorescent polymers. Although macromolecular chains could alleviate the aggregation of fluorophores due to the obstructing effect of macromolecular segments, they are still inclined to aggregate at a high concentration due to their hydrophobic aromatic cores. Accordingly, the ACQ effect and toxicity of fluorescent probes are constant problems in the development of fluorescent bioprobes to detect important biological events in living cells or animals.

Likewise, fluorescent labeling of biomolecules such as proteins and DNA has been attractive for both biomolecular tracing in biological processes and detection and quantization of biomolecules. For biomolecular tracing, the labeling products should be stable for long-term tracing. In addition, the attraction of fluorescent dyes to biomolecules has to be eliminated through a mild labeling protocol with desirable degree of labeling (DOL) so that the labeled biomolecules can maintain their natural folding structures and biological activities. On the other hand, sensitivity of the biomolecule analysis on gel usually depends on the solubility of the stained biomolecules or the background intensity of the stained gel.

Two main methods have been developed for covalent modification of proteins through chemical reactions between reactive groups of fluorescent dyes and special amino acids of proteins. Amine-reactive fluorescent dyes such as fluorescein isothiocyanate (FITC), Cy3 and Cy5 were applied to label lysine (Lys) residues of protein samples and used successfully in immunostaining assays or protein detection on gel.

Thiol-containing proteins were found to play important roles in the biochemical functioning of cells. The amino acid cysteine (Cys) is concerned in catalytic or oxidation/reduction functions of peptides and proteins of which it is a component. A commonly used method is labeling of cysteine (Cys) residues of proteins with alkylating agents.

Fluorescent DNA segments have attracted great interest because of their applications as fluorescent probes for gene detection through fluorescent in situ hybridization (FISH) or hybridization in solutions with the target nucleic acids. Fluorescent dyes can be coupled with an amine or thiol modified nucleoside, nucleotide or oligonucleotide. The fluorescent products can be used to synthesize fluorescent DNA strands for detection of genetic materials in vivo and in vitro.

Fluorescent labeling of biomolecules with water soluble dyes through their charge-charge interaction also has many advantages such as easy handling and fast detection.

However, all the binding aggregation-caused-quenching (ACQ) dyes face the self-quenching problem when the fluorophore to protein ratio (F/P ratio) is over a certain level. Moreover, the poststaining method is employed by most traditional fluorescent dyes while protein labeling requires the labeled proteins to be fixed with dilute acetic acid. This inhibits the transfer of the proteins on the gel to the nitrocellulose membranes for further analysis during western blotting. Also, the DOL of the fluorescent DNA prepared with traditional fluorescent dyes must be controlled at a relatively low level to avoid quenching of fluorescence, and thus the sensitivity of the probes is significantly weakened.

Accordingly, there is a great need for the development of fluorescent bioprobes that exhibit aggregation induced emission (AIE). In addition, there is a need for fluorescent bioprobes that are not limited by the F/P ratio restriction, thereby allowing the use of relatively high concentrations of fluorophores in both prestaining and poststaining methods. Furthermore, there is a need for fluorescent bioprobes that are highly biologically compatibility, nontoxic to live cells, do not interfere with the cell physiology and proliferation, resistant to photobleaching, and have the ability to stay inside live cells for a long period of time without leaking out into the culture media.

SUMMARY

The present subject matter is directed to novel fluorescent bioprobes comprising fluorogens labeled on biomolecules that exhibit aggregation-induced emission (AIE), meaning they are emissive in the solid state. Moreover, the AIE characteristics of the fluorogens make the fluorescent bioprobe easy to handle and use. In addition, the AIE fluorogens are nontoxic to live cells and do not interfere with cell physiology and proliferation. Furthermore, in comparison to conventional fluorogens, AIE fluorogens eliminate the F/P ratio restriction, allowing the use of relatively high concentrations of fluorophore in both prestaining and poststaining methods. Since both staining methods require no fixation, the stained biomolecules (proteins, DNA, etc.) can be further analyzed. Furthermore, the fluorescence intensities of the labeled biomolecules increase linearly with the increasing concentration of fluorogens.

In one embodiment, the present subject matter is directed to a fluorescent bioprobe comprising one or more fluorogens labeled on biomolecules; wherein the fluorescent bioprobe emits fluorescence; wherein the fluorogens exhibit aggregation-induced emission and comprise a backbone structure selected from the group consisting of:

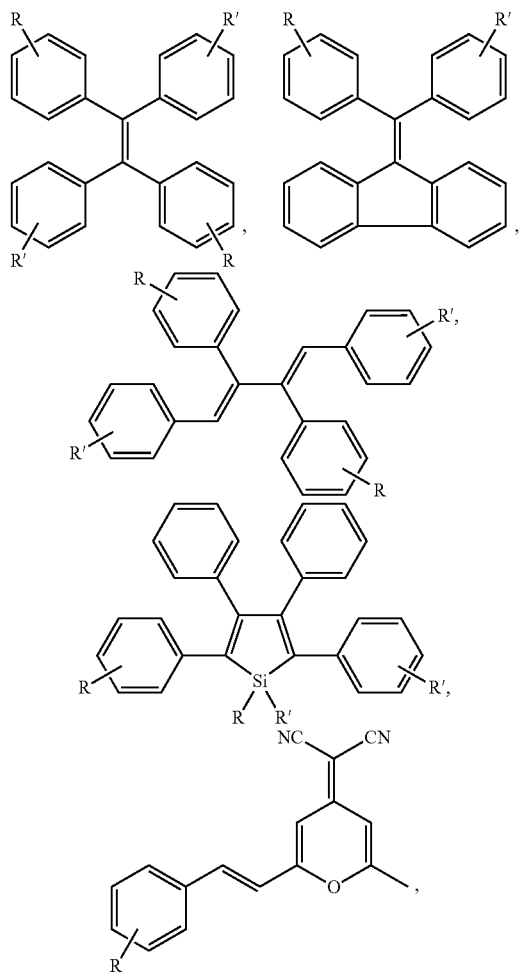

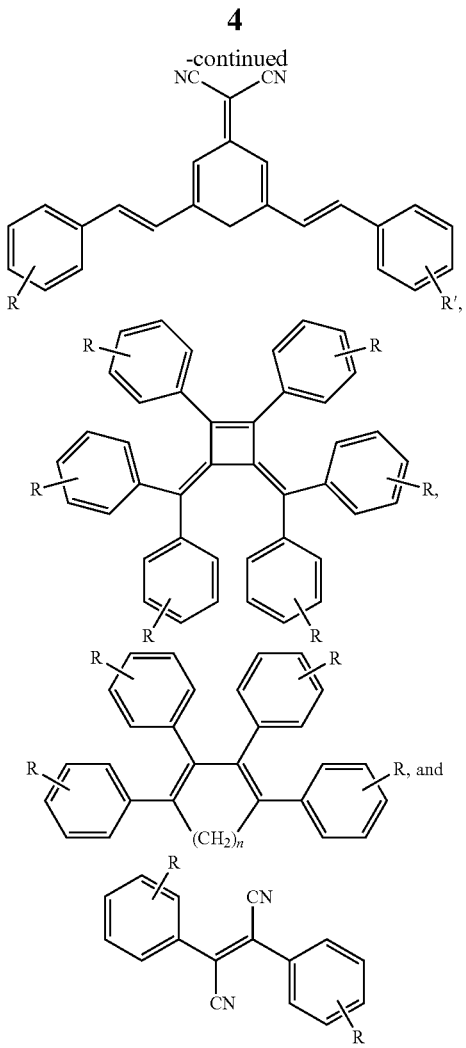

wherein: each R and R' are independently selected from the group consisting of: H, $C_nH_{2n+1}$, $OC_nH_{2n+1}$, $C_6H_5$, $OC_6H_5$, and $(X)_nN[(CH_2)_mCH_3]_2$; X is selected from the group consisting of $(CH_2)_n$, $C_6H_5$, and $O(CH_2)_n$; and n, m independently=an integer from 0 to 20.

In another embodiment, the present subject matter relates to a fluorescent bioprobe comprising one or more fluorogens, described above, labeled on chitosan. In this embodiment, the fluorescent bioprobes emit much brighter luminescence because the rotations of AIE fluorogens are restricted and block the nonradioactive relaxation channel and populate the radioactive decay. In addition, the fluorescent chitosan bioprobes can stain the cell much better than ACQ molecules, and they were retained in live cells without leakage because the fluorogen labeled chitosan macromolecular chains have strong binding ability to the cell cytoplasmic region via electrostatic attractions, hydrogen bonding, and/or hydrophobic interactions. Furthermore, the present subject matter relates to the use of fluorescent chitosan bioprobes for cell imaging, including long-term cell tracing.

The present subject matter also relates to a method of preparing such fluorescent bioprobes comprising the following steps: (i) synthesizing the fluorogens with one or more amine- or thiol-reactive functional groups; and (ii) labeling the biomolecules with the fluorogens via a reaction between the fluorogens and one or more amine or thiol groups of the biomolecules.

In addition, the present subject matter relates to a method of labeling and detecting DNA with the fluorescent bioprobe through enzymatic incorporation of the fluorescent bioprobe into DNA and detecting fluorescence. In this embodiment, the fluorogens are labeled onto biomolecules including nucleosides, nucleotides, and oligonucleotides. In addition, the fluorescent bioprobes can be incorporated enzymatically into DNA strains with a degree of labeling (DOL) up to the theoretic limit.

Furthermore, the present subject matter relates to a method of labeling and detecting proteins comprising: (i) synthesizing one or more fluorogens with one or more amine- or thiol-reactive functional groups; and (ii) labeling the proteins with the fluorogens via a reaction between the fluorogens and one or more amine or thiol groups of the proteins.

Finally, the present subject matter is also directed to a method of in vitro cell imaging comprising: (a) contacting cells with the fluorescent bioprobe; and (b) detecting cellular fluorescence via fluorescent microscopy. In one embodiment, the fluorescent bioprobes can be used for live cell tracking via fluorescent microscopy. Due to the excellent fluorescent and cytophilic properties of the fluorescent bioprobes, they can be used widely in the bioimaging field, including diagnosis of cancer and drug metabolism.

BRIEF DESCRIPTION OF THE DRAWINGS

The file of this patent contains at least one drawing executed in color. Copies of this patent with color drawing(s) will be provided by the Office upon request and payment of the necessary fee.

Various embodiments will be described in detail with reference to the accompanying drawings.

FIG. 1a illustrates a photoluminescence spectrum of TPENCS in THF/water mixtures with different water fractions ($f_w$). [TPENCS]=10 μM.

FIG. 1b illustrates the photoluminescence peak intensity of TPENCS in aqueous mixtures at different water fractions. TPENCS=10 μM; $\lambda_{em}$=470 nm.

FIG. 2a shows an SDS-PAGE fluorescence image of BSA prestained with TPENCS.

FIG. 2b shows an SDS-PAGE fluorescence image of BSA poststained with TPENCS.

FIG. 2c shows an SDS-PAGE image of BSA restained with Coomassie R-250.

FIG. 29a1 shows a bright-field image of HeLa cells cultured in absence of chitosan and TPEITC-CS.

FIG. 29b1 shows a bright-field image of HeLa cells cultured in presence of chitosan.

FIG. 29c1 shows a bright-field image of HeLa cells cultured in presence of TPEITC-CS with the molar feed ratio of dye/CS (1/100).

FIG. 29d1 shows a bright-field image of HeLa cells cultured in presence of TPEITC-CS with the molar feed ratio of dye/CS (5/100).

FIG. 29e1 shows a bright-field image of HeLa cells cultured in presence of TPEITC-CS with the molar feed ratio of dye/CS (20/100).

FIG. 29a2 shows a fluorescent image of HeLa cells cultured in absence of chitosan and TPEITC-CS.

FIG. 29b2 shows a fluorescent image of HeLa cells cultured in presence of chitosan.

FIG. 29c2 shows a fluorescent image of HeLa cells cultured in presence of TPEITC-CS with the molar feed ratio of dye/CS (1/100).

FIG. 29d2 shows a fluorescent image of HeLa cells cultured in presence of TPEITC-CS with the molar feed ratio of dye/CS (5/100).

FIG. 29e2 shows a fluorescent image of HeLa cells cultured in presence of TPEITC-CS with the molar feed ratio of dye/CS (20/100).

DETAILED DESCRIPTION

Definitions

Figure 1:
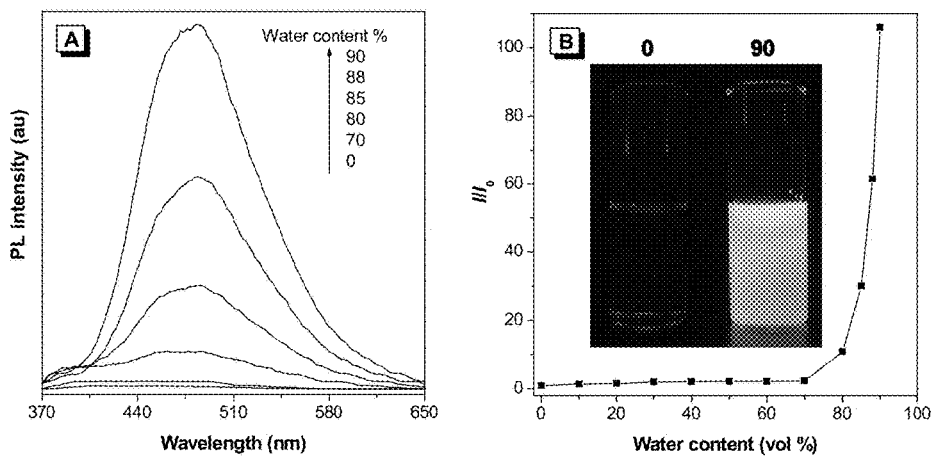

All technical and scientific terms used herein have the same meanings as commonly understood by someone ordinarily skilled in the art to which the present subject matter belongs. The following definitions are provided for clarity.

The phrase "π-conjugated fluorogen" as used herein refers to any fluorogen covalently bonded with alternating single and double bonds in an organic compound.

The term "$\lambda_{ex}$" as used herein refers to excitation wavelength.

The phrase "aggregation caused quenching" or "ACQ" as used herein refers to the phenomenon wherein the aggregation of π-conjugated fluorogens significantly decreases the fluorescence intensity of the fluorogens. The aggregate formation is said to "quench" light emission of the fluorogens.

The phrase "aggregation induced emission" or "AIE" as used herein refers to the phenomenon manifested by compounds exhibiting enhancement of light-emission upon aggregation in the amorphous or crystalline (solid) states whereas they exhibit weak or almost no emission in dilute solutions.

The term "biomacromolecule" as used herein refers to a very large molecule, such as a protein, nucleic acid, or polysaccharide of biological origin.

The term "DMF" as used herein refers to dimethylformamide, which is an organic compound with the formula $(CH_3)_2NC(O)H$. It is a common solvent for chemical reactions.

The term "DMSO" as used herein refers to dimethyl sulfoxide, which is an organic compound having the formula $(CH_3)_2SO$. It is a common solvent for chemical reactions.

The term "EDTA" as used herein refers to ethylenediaminetetraacetic acid. It is a polyamino carboxylic acid and a colorless, water-soluble solid.

The phrase "emission intensity" as used herein refers to the magnitude of fluorescence/phosphorescence normally obtained from a fluorescence spectrometer or a fluorescence microscopy measurement.

The term "fixation" as used herein refers to a process with which a biomolecule is denatured and fixed on polyacrylamide gel. The fixation buffer is typically composed of water, acetic acid, and methanol. For example, the fixation buffer might comprise 50% water, 10% acetic acid, and 40% methanol.

The term "fluorogen" as used herein refers to a chemical compound that manifests luminescence.

The phrase "quantum dots" as used herein refers to a type of matter, i.e., a semiconductor, whose excitons are confined in all three spatial dimensions. Quantum dots can be semiconductors whose electronic characteristics are closely related to the size and shape of the individual crystal. Generally, the smaller the size of the crystal, the larger the band gap, i.e., the difference in energy between the highest valence band and the lowest conduction band becomes greater. Therefore more energy is needed to excite the dot, and concurrently, more energy is released when the crystal returns to its resting state.

The term "a" or "an" as used herein includes the singular and the plural, unless specifically stated otherwise. Therefore, the term "a," "an," or "at least one" can be used interchangeably in this application.

Throughout the application, descriptions of various embodiments use the term "comprising;" however, it will be understood by one of skill in the art, that in some specific instances, an embodiment can alternatively be described using the language "consisting essentially of" or "consisting of."

For the purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to nonemissive dyes with propeller-like molecular structures such as tetraphenylethene (TPE) and silole which are induced to emit efficiently in aggregate formation. Mechanistic investigations reveal that the AIE is caused by the restriction to the intramolecular rotations of the luminogens in the aggregate state, which blocks the nonradiative channels and populates the radiative decay.

The AIE effect makes the fluorescent bioprobes easy to handle and use. Moreover, the AIE fluorogens are nontoxic to live cells and do not interfere with cell physiology or proliferation. In addition, in comparison to conventional fluorogens, the present AIE fluorogens eliminate the F/P ratio restriction, thereby allowing the use of relatively high concentrations of fluorophore in both prestaining and poststaining methods. Since both staining methods require no fixation procedure, the stained proteins can be further analyzed. Also different from the conventional fluorogens, the AIE fluorogen labeled dNTPs can be incorporated enzymatically into DNA strands with the degree of labeling (DOL) up to the theoretic limit. In addition, the fluorescence intensities of the labeled biomolecules increase linearly along with the increasing concentration of AIE fluorogens. Given outstanding labeling effects, the present subject matter is also directed to methods of detecting and labeling biomolecules with AIE fluorogens.

Accordingly, the present subject matter is directed to a fluorescent bioprobe comprising one or more fluorogens labeled on biomolecules; wherein the fluorescent bioprobe emits fluorescence; wherein the fluorogens exhibit aggregation-induced emission and comprise a backbone structure selected from the group consisting of:

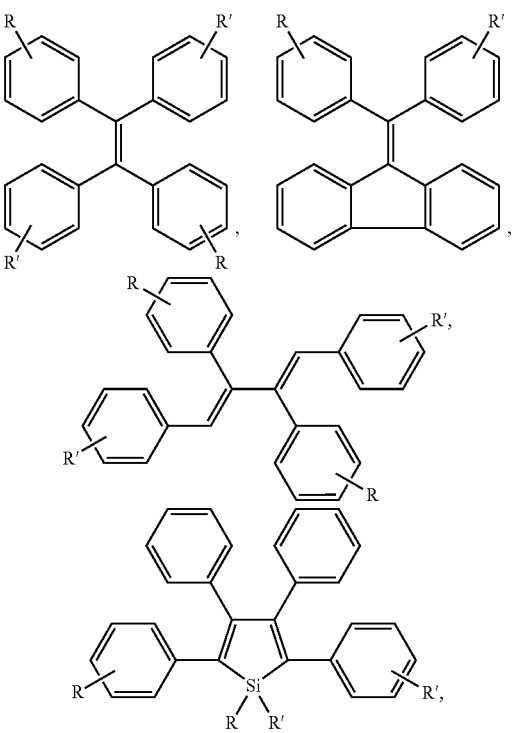

-continued

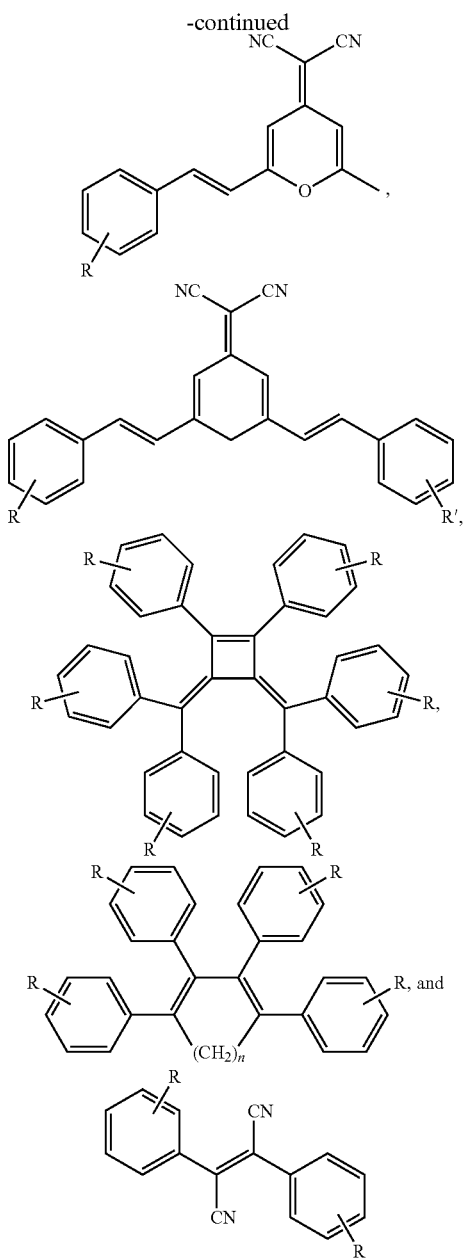

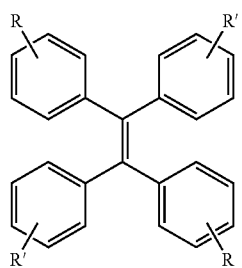

wherein each R and R' are independently selected from the group consisting of: H, $C_nH_{2n+1}$, $OC_nH_{2n+1}$, $C_6H_5$, $OC_6H_5$, and $(X)_nN[(CH_2)_mCH_3]_2$; X is selected from the group consisting of $(CH_2)_n$, $C_6H_5$, and $O(CH2)_n$; and n, m independently=an integer from 0 to 20.

Accordingly, in one embodiment, the fluorogens of the fluorescent bioprobe comprise a backbone structure represented by formula (I):

(I)

wherein each R and R' are independently selected from the group consisting of: H, $C_nH_{2n+1}$, $OC_nH_{2n+1}$, $C_6H_5$, $OC_6H_5$, and $(X)_nN[(CH_2)_mCH_3]_2$; X is selected from the group consisting of $(CH_2)_n$, $C_6H_5$, and $O(CH2)_n$; and n, m independently=an integer from 0 to 20.

In an alternative embodiment, the fluorogens of the fluorescent bioprobe comprise a backbone structure represented by formula (II):

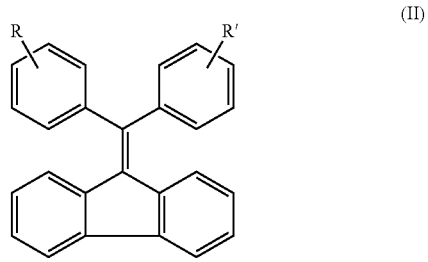

(II)

wherein R and R' are independently selected from the group consisting of: H, $C_nH_{2n+1}$, $OC_nH_{2n+1}$, $C_6H_5$, $OC_6H_5$, and $(X)_nN[(CH_2)_mCH_3]_2$; X is selected from the group consisting of $(CH_2)_n$, $C_6H_5$, and $O(CH2)_n$; and n, m independently=an integer from 0 to 20.

In another embodiment, the fluorogens of the fluorescent bioprobe comprise a backbone structure represented by formula (III):

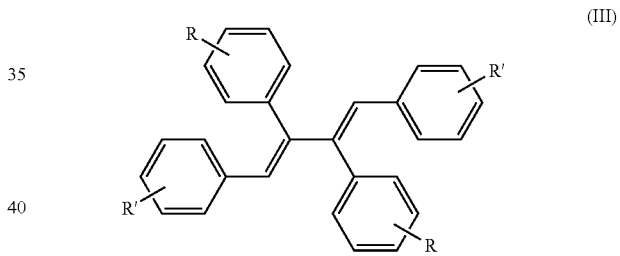

(III)

wherein each R and R' are independently selected from the group consisting of: H, $C_nH_{2n+1}$, $OC_nH_{2n+1}$, $C_6H_5$, $OC_6H_5$, and $(X)_nN[(CH_2)_mCH_3]_2$; X is selected from the group consisting of $(CH_2)_n$, $C_6H_5$, and $O(CH2)_n$; and n, m independently=an integer from 0 to 20.

In an alternative embodiment, the fluorogens of the fluorescent bioprobe comprise a backbone structure represented by formula (IV):

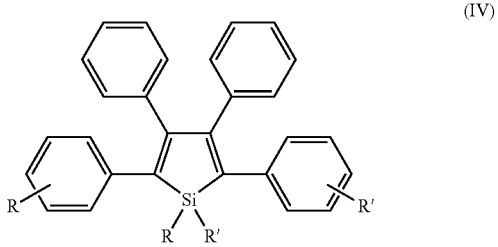

(IV)

wherein each R and R' are independently selected from the group consisting of: H, $C_nH_{2n+1}$, $OC_nH_{2n+1}$, $C_6H_5$, $OC_6H_5$, and $(X)_nN[(CH_2)_mCH_3]_2$; X is selected from the group consisting of $(CH_2)_n$, $C_6H_5$, and $O(CH2)_n$; and n, m independently=an integer from 0 to 20.

In another embodiment, the fluorogens of the fluorescent bioprobe comprise a backbone structure represented by formula (V):

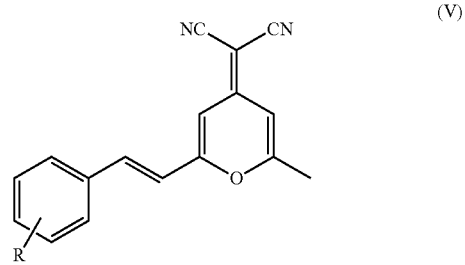
(V)

wherein R is independently selected from the group consisting of: H, $C_nH_{2n+1}$, $OC_nH_{2n+1}$, $C_6H_5$, $OC_6H_5$, and $(X)_nN[(CH_2)_mCH_3]_2$; X is selected from the group consisting of $(CH_2)_n$, $C_6H_5$, and $O(CH2)_n$; and n, m independently=an integer from 0 to 20.

In a different embodiment, the fluorogens of the fluorescent bioprobe comprise a backbone structure represented by formula (VI):

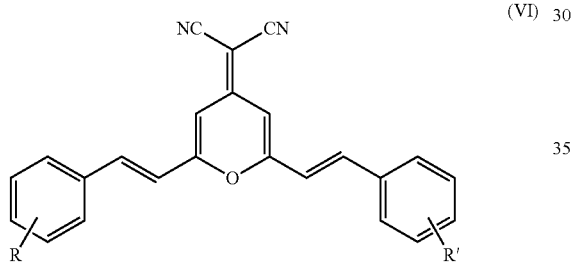
(VI)

wherein R and R' are independently selected from the group consisting of: H, $C_nH_{2n+1}$, $OC_nH_{2n+1}$, $C_6H_5$, $OC_6H_5$, and $(X)_nN[(CH_2)_mCH_3]_2$; X is selected from the group consisting of $(CH_2)_n$, $C_6H_5$, and $O(CH2)_n$; and n, m independently=an integer from 0 to 20.

In an alternative embodiment, the fluorogens of the fluorescent bioprobe comprise a backbone structure represented by formula (VII):

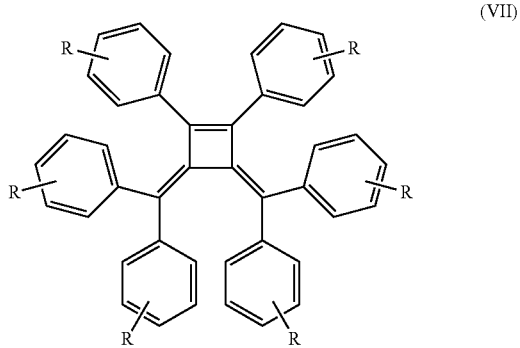
(VII)

wherein each R is independently selected from the group consisting of: H, $C_nH_{2n+1}$, $OC_nH_{2n+1}$, $C_6H_5$, $OC_6H_5$, and $(X)_nN[(CH_2)_mCH_3]_2$; X is selected from the group consisting of $(CH_2)_n$, $C_6H_5$, and $O(CH2)_n$; and n, m independently=an integer from 0 to 20.

In another embodiment, the fluorogens of the fluorescent bioprobe comprise a backbone structure represented by formula (VIII):

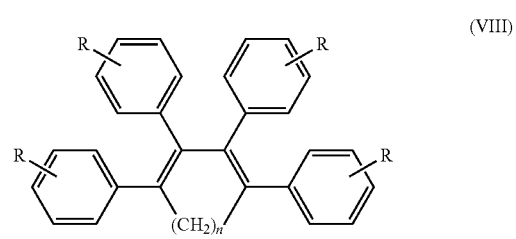
(VIII)

wherein each R is independently selected from the group consisting of: H, $C_nH_{2n+1}$, $OC_nH_{2n+1}$, $C_6H_5$, $OC_6H_5$, and $(X)_nN[(CH_2)_mCH_3]_2$; X is selected from the group consisting of $(CH_2)_n$, $C_6H_5$, and $O(CH2)_n$; and n, m independently=an integer from 0 to 20.

Alternatively, the fluorogens of the fluorescent bioprobe can comprise a backbone structure represented by formula (IX):

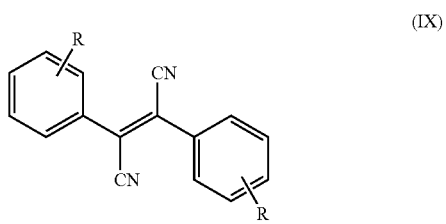
(IX)

wherein each R is independently selected from the group consisting of: H, $C_nH_{2n+1}$, $OC_nH_{2n+1}$, $C_6H_5$, $OC_6H_5$, and $(X)_nN[(CH_2)_mCH_3]_2$; X is selected from the group consisting of $(CH_2)_n$, $C_6H_5$, and $O(CH2)_n$; and n, m independently=an integer from 0 to 20.

Labeling the fluorogens onto biomacromolecules that can be bioconjugated with cells is one way to keep the fluorescent bioprobes in the cells for cell imaging. The macromolecules chosen for fixing the dyes should be biocompatible and have abundant hydroxyl groups and/or amino groups that are beneficial for the labeling reactivity and hydrophilicity.

In one embodiment, the biomolecules on which the fluorogens are labeled can be one or more selected from the group consisting of proteins, modified nucleosides, modified nucleotides, modified oligonucleotides, DNA, chitosan, molecules containing primary amine groups, and molecules containing primary thiol groups.

In a preferred embodiment, the biomolecule on which the fluorogens are labeled is chitosan. Chitosan (CS), a renewable natural biopolymer, is one kind of linear polysaccharide made up of glucosamine and N-acetylglucosamine units linked by 1-4 glycosidic bonds, and widely used in biomedical fields due to its unique biocompatible and biodegradable properties. The many hydroxyl and amino groups on chitosan macromolecules are easily labeled by AIE fluorogens. Moreover, chitosan is known to interact with cell membranes through nonspecific electrostatic attractions, in addition to hydrogen bonding and hydrophobic interactions. This contributes significantly to the adhesion of chitosan molecules to the cells, so chitosan-based bioprobes could bind the cell cytoplasmic region strongly, and have promising applications in tumor diagnosis, long-term cell tracing, and drug metabolism. In one embodiment, the fluorogen labeled chitosan bioprobe has a structure represented by formula (X):

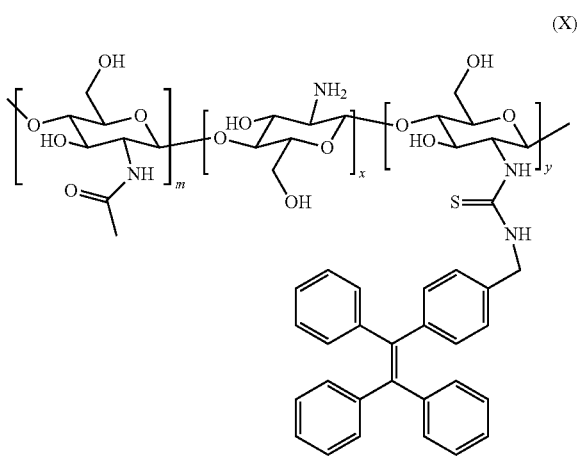

In one embodiment, AIE fluorogens with functional groups, such as isothiocyanates and aldehydes, were synthesized and used to label chitosan macromolecular chains. Since many AIE fluorogens can be labeled on the chitosan macromolecular chains, the resulting fluorescent bioprobe emitted much brighter fluorescence. This is because the rotations of AIE fluorogens are restricted and block the nonradioactive relaxation channel and populate the radioactive decay. AIE-CS is pH sensitive, due to the precipitation and contraction of macromolecular chains when the AIE-CS solution is changed from acidic to basic, resulting in the activation of AIE, whereby the solution becomes brighter. AIE-CS can stain cells much better than ACQ molecules, and is retained in live cells without leakage because AIE-CS has a strong binding ability to the cell cytoplasmic region through electrostatic attractions, hydrogen bonding, and hydrophobic interactions, etc. The highly emissive and leakage-free properties of AIE-CS enable them to be used for long-term cell tracing. In fact, HeLa cells stained by AIE-CS could still be detected after 15 passages. The excellent fluorescence properties and cytophilic properties of the fluorogen labeled chitosan make the fluorescent bioprobes ideal for a wide number of uses in the bioimaging field, such as diagnosis of early cancer and drug metabolism.

Accordingly, the present subject matter also relates to a fluorogen labeled chitosan bioprobe exhibiting excellent AIE, permeability, and biocompatibility. Therefore, the fluorogen labeled chitosan does not exhibit aggregation induced quenching. In addition, the present subject matter relates to a fluorogen labeled chitosan solution which effectively stains the cytoplasmic areas of cells, such as mammalian cells. In a particular embodiment, the fluorogen labeled chitosan can be used in large quantities and stay inside live cells for a long period of time without leakage. In another embodiment, the fluorogen labeled chitosan bioprobe can be used for in vitro imaging. In a further embodiment, the fluorogen labeled chitosan bioprobe can be used for living cell tracking.

In addition, the present subject matter is directed to AIE fluorogens that are designed and synthesized with an amine- or thiol-reactive functional group or functional groups which make the fluorogens water soluble. Amine-reactive AIE fluorogens used for labeling Lys residue of proteins can be used through both prestaining method and poststaining methods. The fluorescence intensities of labeled proteins detected on the gel increase linearly with the increasing amount of fluorogens. Multiple samples can be stained at the same time and no fixation is needed during the labeling process. Therefore, the proteins labeled on the gel can be transferred onto nitrocellulose membrane for further analysis.

Cys residue of protein samples can be stained by the thiol-reactive AIE fluorogens. The fluorescence intensity of the fluorogens may be enhanced due to the elimination of the internal heavy atom effect. Optimal labeling time and temperature of Cys residues can enable the maintenance of protein structures. The concentration of thiol reactive AIE polyenes should be controlled to avoid the nonspecific labeling. Reducing reagents and denaturants also play important roles during the Cys labeling.

Fluorescent DNA fragments can be obtained by incorporation of AIE fluorogen labeled dNTPs onto DNA products through various enzymatic incorporation methods. The DOL values of AIE fluorogen labeled DNA are either comparable to the traditional fluorogen labeled ones through nick translation and random priming or are much higher (~5 times) through PCR. The bp numbers of templates play an important role during enzymatic incorporation. DOL values of fluorescent DNA products labeled with an AIE fluorogen can be precisely controlled. In contrast to the FITC and 5-BMF, which always exhibit aggregation-caused-quenching (ACQ) at high concentrations, the AIE fluorogen can be used to label biomolecules concentrations as high as possible. In addition, the fluorescence intensity of the AIE fluorogens labeled on biomolecules continues to increase linearly with the increase in fluorogen concentration. Water soluble AIE fluorogens can also be used to label biomolecules physically in aqueous media and enable fast detection of the biomolecules.

Accordingly, the present subject matter is also directed to a method of preparing a fluorescent bioprobe comprising the following steps: (i) synthesizing the fluorogens with one or more amine- or thiol-reactive functional groups; and (ii) labeling the biomolecules with the fluorogens via a reaction between the fluorogens and one or more amine or thiol groups of the biomolecules. In a preferred embodiment, the labeling is carried out without a fixation process and without self-quenching.

In one embodiment, amine- or thiol-reactive functional groups comprise a lower alkyl group of 1-4 carbons and can be selected from the group consisting of isocyanates, isothiocyanates, aldehydes, succinimidyl esters, carboxylic acids, 4-sulfotetrafluorophenyl esters, 2,4,5,6-tetrafluorophenyl esters, sulfodicholorphenol esters, carbonyl azides, sulfonyl chlorides, haloacetamides, and maleimides.

The fluorogens with one or more amine- or thiol-reactive functional groups can be one or more selected from the group consisting of:

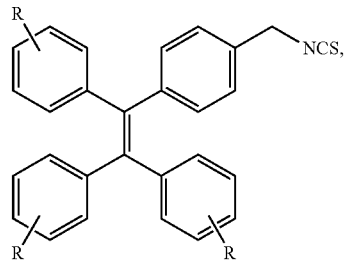

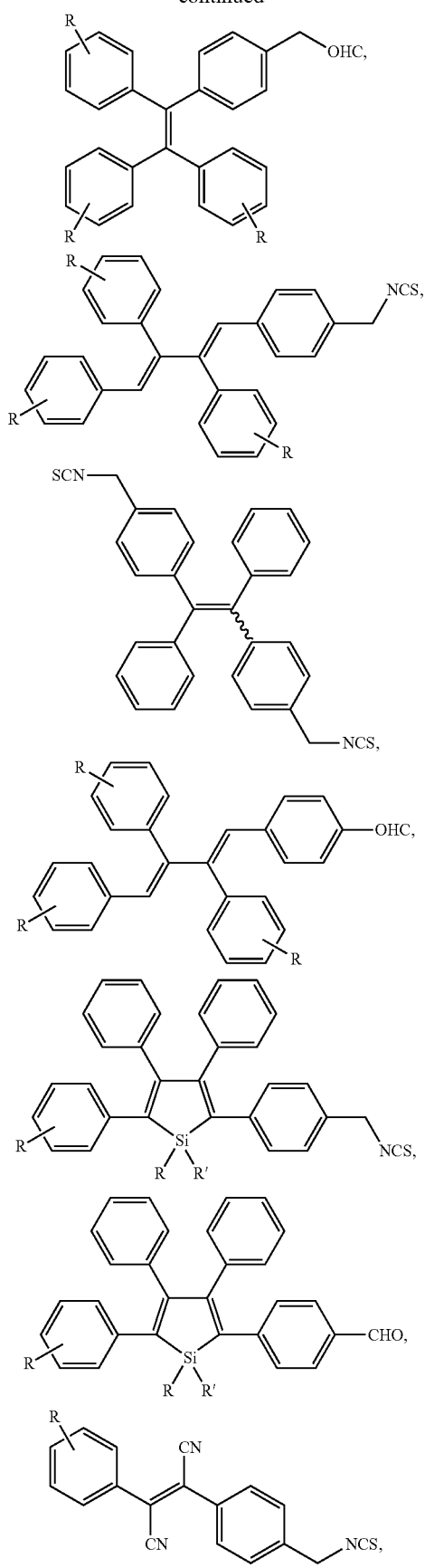

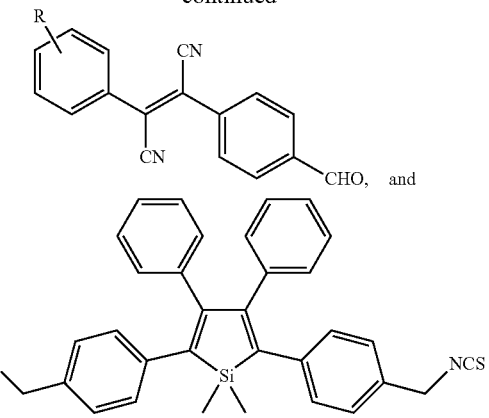

wherein each R is independently selected from the group consisting of: H, $C_nH_{2n+1}$, $OC_nH_{2n+1}$, $C_6H_5$, $OC_6H_5$, and $(X)_nN[(CH_2)_mCH_3]_2$; X is selected from the group consisting of $(CH_2)_n$, $C_6H_5$, and $O(CH2)_n$; and n, m independently=an integer from 0 to 20.

Compared with the more reactive isocyanate compounds, isothiocyanate products are more stable in water and in most organic solvents, but have a comparable reactivity with the amine groups of proteins. In one embodiment the fluorogen with one or more amine- or thiol-reactive functional groups is 1,2-bis[4-(isothiocyanatemethyl)phenyl]-1,2-diphenylethene (TPENCS), which has a structure represented by formula (XI):

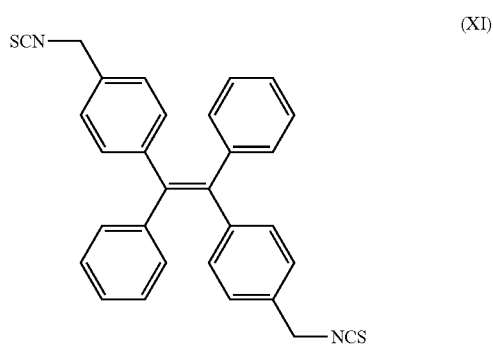

(XI)

The AIE of TPENCS is illustrated in FIG. 1. Similar to all other AIE molecules, TPENCS was weakly emissive in good solvents such as THF, while the addition of water, a relative non-solvent, dramatically increased its emission efficiency (FIG. 1a). With water content ranging from 0-70%, the fluorescence intensity remained at a very low level. When the water concentration was in the 80-90 vol % range, a rapid and dramatic increase of the fluorescence intensity with increasing water content was observed (FIG. 1b). The PL intensity of TPENCS in the water/THF solution with a water fraction of 90 vol % was approximately 50-fold higher than that in the mixture with 70% water. The quantum efficiency of TPENCS was 52.2% in the solid state.

In another embodiment, the fluorogen is 1-[4-bromophenyl]-1,2,2-triphenylethene (TPEMBR), which has a structure represented by formula (XII):

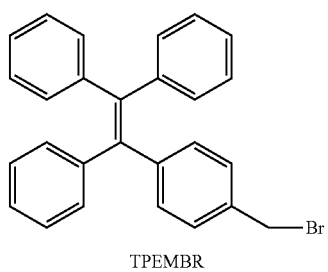

TPEMBR (XII)

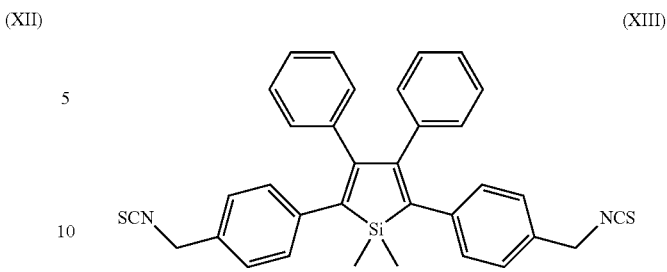

(XIII)

Figure 9:
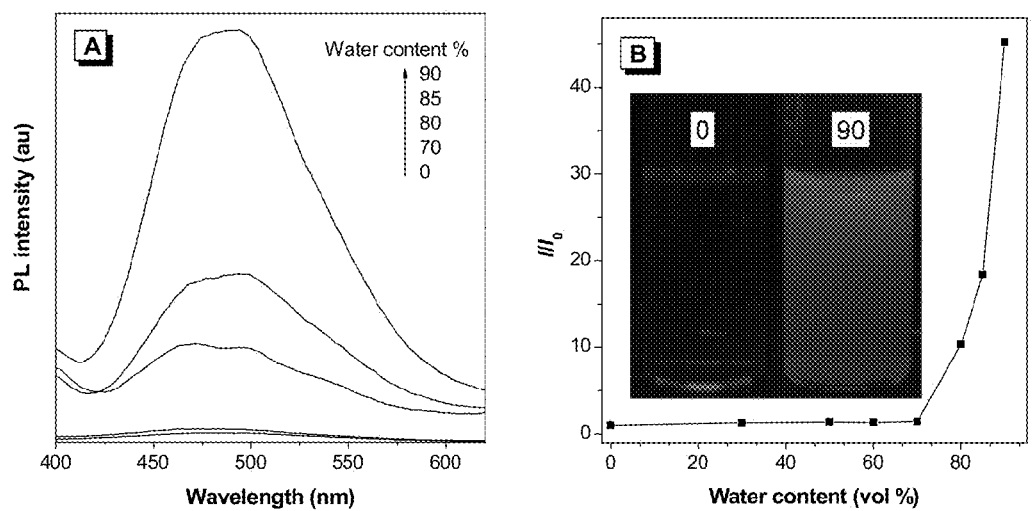
FIG. 9a illustrates a photoluminescence spectrum of TPEMBR in THF/water mixtures with different water fractions ($f_w$). [TPEMBR]=10 μM.
FIG. 9b illustrates the photoluminescence peak intensity of TPEMBR in aqueous mixtures at different water fractions. TPEMBR=10 μM; $\lambda_{em}$=470 nm.
Figure 10:
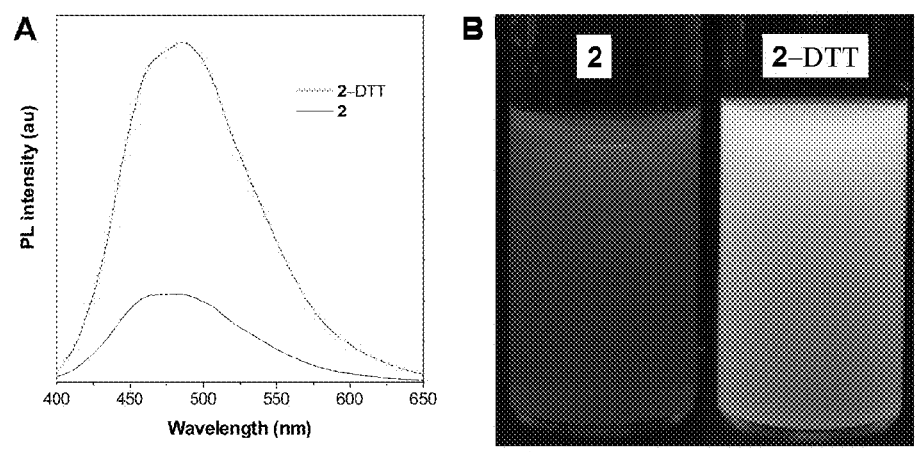
FIG. 10a illustrates the photoluminescence spectrum of TPEMBR in THF/water mixtures before and after reaction with DTT. [TPEMBR]=10 μM.
FIG. 10b shows a fluorescence image of TPEMBR in THF/water mixtures before and after reaction with DTT. [TPEMBR]=10 μM.

In comparison with other alkyl halides such as iodomethyl, bromomethyl groups in water and most organic solvents exhibit high stability with respect to light and temperature while maintaining reactivity with thiol groups. As shown in FIG. 9, TPEMBR exhibited AIE. Similar to other AIE active molecules, TPEMBR only gave weak emission in good solvents such as THF. Upon the addition of a large amount of water (>70 vol %) into the solution, the emission efficiency of TPEMBR was dramatically increased (FIG. 9a). To quantify the effect of water content on the degree of fluorescent emission enhancement, the photoluminescence intensity of TPEMBR was measured where the fraction of water was increased from 0 to 90 vol %. With the water content in the range of 0-70%, the fluorescent intensity remained at a very low level. With the water fraction reaching the 80-90 vol % range, a rapid and dramatic increase of the fluorescent intensity was observed (FIG. 9b). The photoluminescence intensity of TPEMBR in the water/THF solution with a water fraction of 90 vol % was approximately 50-fold stronger than that in the mixture with 70% water. In the solid state, the quantum efficiency of TPEMBR was determined to be 31.7%.

Figure 12:
FIG. 12a shows an SDS-PAGE fluorescence image of BSA stained with various concentrations of TPEMBR.
FIG. 12b shows an image of the gel of BSA stained with various concentrations of TPEMBR restained with Coomassie R-250.

In addition to the enhancement of fluorescence because of its AIE property, TPEMBR becomes even more emissive through the reaction between its bromomethyl group and thiol group of proteins, presumably due to the elimination of the internal heavy atom effect of bromide. Dithiothreitol (DTT) was selected in the model reactant to react with TPEMBR to demonstrate this fluorescence enhancement effect. TPEMBR and DTT in equal amount were dissolved in THF to give a concentration of 10 μM for each component. The mixture was then incubated at room temperature overnight. Photoluminescence intensity and UV absorption of TPEMBR were measured in THF/water mixtures with a water fraction of 90 vol % before and after reacting with DTT. As shown in FIGS. 12a and 12b, the quantum efficiency of TPEMBR in the water/THF solution with a water fraction of 90 vol % was approximately 3 times higher after reacting with DTT. The signal-to-noise ratio also improved a lot as a result of this double-enhancement effect.

Figure 17:
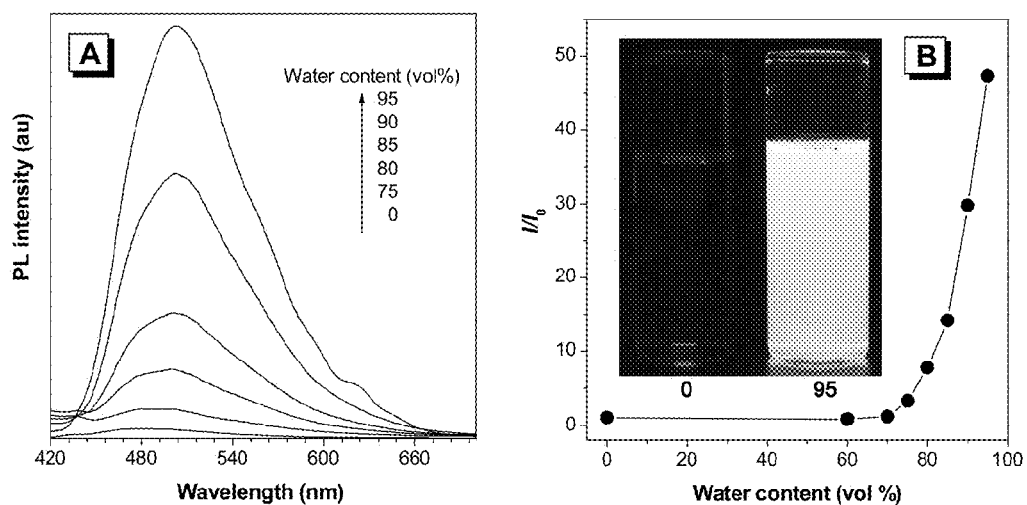
FIG. 17a illustrates a photoluminescence spectrum of SITC in THF/water mixtures with different water fractions ($f_w$). [SITC]=10 μM.
FIG. 17b illustrates the photoluminescence peak intensity of SITC in an aqueous mixture versus the water fraction of the aqueous mixtures. [SITC]=10 μM; $\lambda_{em}$=510 nm.

In another embodiment, the one or more amine- or thiol-reactive functional groups is the silole derivative, 1,1-dimethyl-2,5-bis[4-(isothiocyanatemethyl)phenyl]-3,4-diphenyl silole (SITC), which has a structure represented by formula (XIII):

The AIE of SITC is illustrated in FIGS. 17a and 17b. The wavelength at maximum absorption of SITC was at 363 nm and the emission maximum was at 490 nm. Similar to all other AIE molecules, SITC was weakly emissive in good solvents such as THF, while the addition of a large amount of water (>70 vol %) into the solution dramatically increased its emission efficiency (FIG. 17a). To quantify the effect of water content on the elevation of the fluorescent emission, the photoluminescence intensity of SITC was measured with concentration of water increasing from 0 to 90 vol %. With water content ranging from 0-70%, the fluorescent intensity remained at a very low level. When the water concentration was in the 80-95 vol % range, a rapid and dramatic increase of the fluorescent intensity with increasing water content was observed (FIG. 17b). The photoluminescence intensity of SITC in the water/THF solution with a water fraction of 95 vol % was approximately 50-fold higher than that in the mixture with 70% water. The quantum efficiency of SITC was 45.8% in the solid state. Compared with the reactive isocyanate compounds, isothiocyanate products are more stable in water and most organic solvents, but have a comparable reactivity with the primary amine groups.

The present subject matter also relates to a method for labeling and detecting DNA with the fluorescent bioprobe comprising enzymatically incorporating the fluorescent bioprobe into DNA and detecting fluorescence; wherein the biomolecules are nucleosides, nucleotides, or oligonucleotides.

In one embodiment, amine-reactive AIE polyenes can be used to label various amine-modified dNTPs. Furthermore, the AIE fluorogen labeled dNTPs can be incorporated into DNA products through nick translation and random priming. In addition, the present subject matter is related to AIE fluorogen labeled dNTPs incorporated into DNA products through polymerase chain reaction (PCR) with special bp numbers. In one embodiment, the AIE fluorogen labeled dNTPs can be incorporated into DNA products through PCR with various DNA sequences. Likewise, the AIE fluorogen labeled dNTPs can be incorporated into DNA products through PCR with controllable DOL. In another embodiment, the AIE fluorogen labeled DNA products can be detected on gel or in solutions. Furthermore, the present subject matter is directed to AIE fluorogen labeled DNA products that can be prepared with high DOL without self-quenching.

In one embodiment, the fluorescent bioprobe is an amino-group-containing dUTP5-(3-aminoallyl)-2'-deoxyuridine-5'triphosphate labeled with SITC, which has a structure represented by formula (XIV):

(XIV)

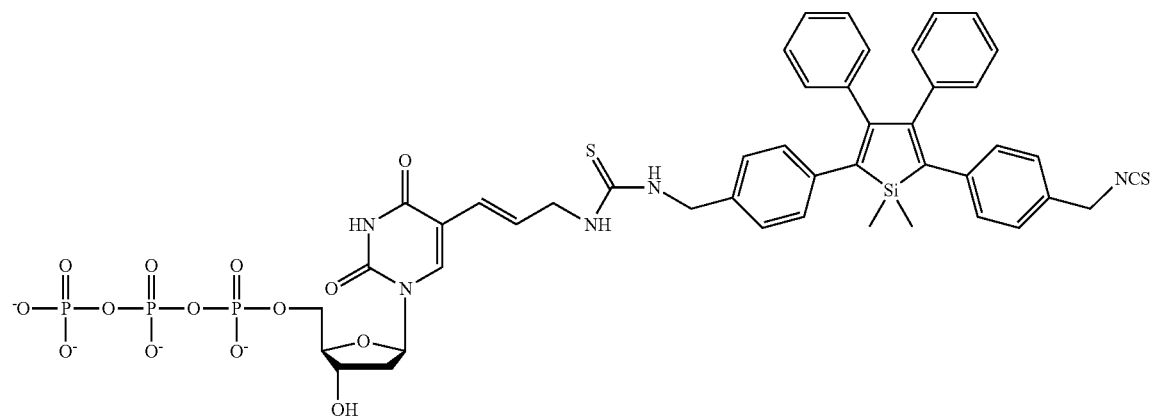

The modification site of aa-dUTP is the C-5 position of the pyrimidine ring, which does not participate in the base-pair hydrogen bonding. To avoid cross-linking of aa-dUTPs by SITC which contains two isothiocyanate groups, a solution of SITC in DMSO was added into aa-dUTP solution with the amount of SITC equal to that of aa-dUTP.

In another embodiment, the present subject matter relates to a method for preparing water soluble fluorogens for the labeling and detection of any biomolecule, wherein the labeling samples consist of any proteins, DNA, or other molecules with biological functions. In addition, the present subject matter relates to water soluble AIE fluorogen labeled DNA products that can be detected on gel or in solutions. The present subject matter also relates to water soluble AIE fluorogens that can be used in high F/P ratios without self-quenching.

In another embodiment, the present subject matter is directed to a method of labeling and detecting proteins comprising: (i) synthesizing one or more fluorogens with one or more amine- or thiol-reactive functional groups; wherein the fluorogens exhibit aggregation-induced emission and comprise a backbone structure selected from the group consisting of:

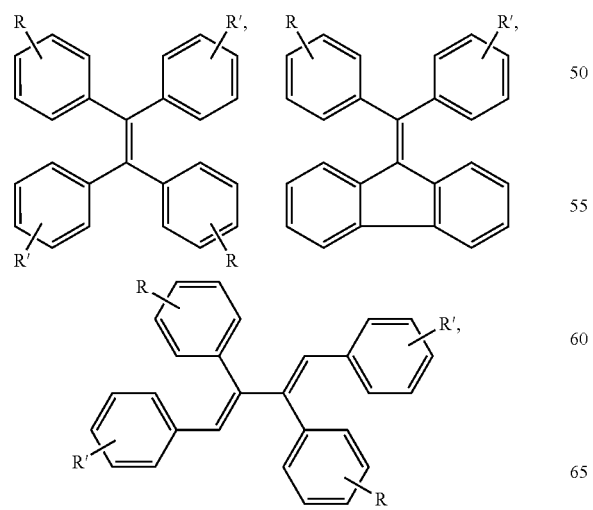

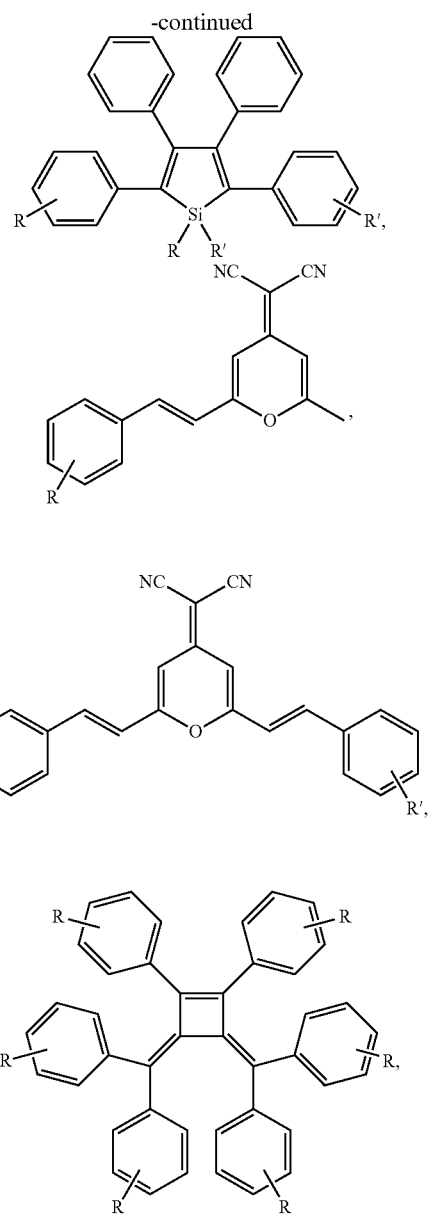

-continued

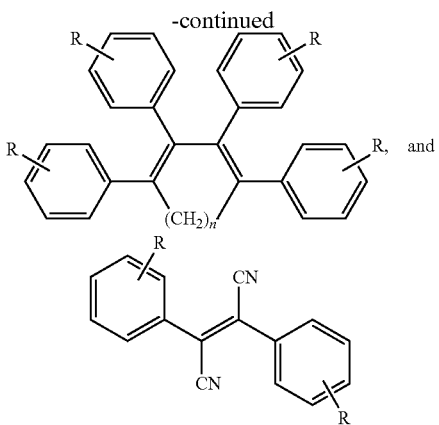

wherein: each R and R' are independently selected from the group consisting of: H, $C_nH_{2n+1}$, $OC_nH_{2n+1}$, $C_6H_5$, $OC_6H_5$, and $(X)_nN[(CH_2)_mCH_3]_2$; X is selected from the group consisting of $(CH_2)_n$, $C_6H_5$, and $O(CH2)_n$; and n, m independently=an integer from 0 to 20; and (ii) labeling the proteins with the fluorogens via a reaction between the fluorogens and one or more amine or thiol groups of the proteins.

In this method, multiple proteins can be labeled with one or more fluorogens simultaneously for detection purposes. In addition, amine-reactive AIE fluorogens can be used in a high F/P ratio without self-quenching. Likewise, thiol-reactive AIE fluorogens can be used in a high F/P ratio without self-quenching. In another embodiment, the AIE fluorogens can be used to label proteins on gel without fixation so that the labeled samples can be transferred onto a nitrocellulose membrane for further analysis. Furthermore, the fluorescence intensity of the AIE fluorogens can be enhanced after labeling with amine- or thiol-containing molecules. The AIE fluorogens can also be used to stain proteins with various labeling times. Various concentrations of the AIE fluorogens can also be used to stain proteins. The AIE fluorogens can be used to stain proteins with various concentrations of reducing agents. Likewise, the AIE fluorogens can be used to stain proteins with various concentrations of denaturants.

In another embodiment, the present subject matter relates to a method of in vitro cell imaging comprising: (a) contacting cells with a fluorescent bioprobe described herein; and (b) detecting cellular fluorescence via fluorescent microscopy. In one embodiment, the fluorescent microscopy can be used for live cell tracking. In cell imaging, the cells uptake the fluorescent bioprobe and the fluorogens interact with biomolecules inside cells via electrostatic attraction, hydrogen bonding, or hydrophobic interaction.

EXAMPLES

Having described the subject matter, the following examples are given to illustrate various embodiments and specific applications of the present subject matter. These specific examples are not intended to limit the scope of the subject matter described in this application.

Example 1

Synthesis of TPENCS, TPEMBR, and SITC

Materials & Equipment:
Tetrahydrofuran (THF; Labscan) was distilled under nitrogen from sodium benzophenone ketyl immediately prior to use. Acrylamide was purchased from Bio-Rad. Aminoallyl-dUTP (aa-dUTP), dNTPs, DNase I (RNase-free), DNA Polymerase I, Klenow Fragment exo-, Random Hexamer Primer, Long PCR Enzyme Mix and GeneJET™ PCR Purification Kit, GeneRuler™ 100 bp Plus DNA Ladder (ready-to-use, 100-3000 bp), 6×DNA Loading Dye were purchased from Fermentas (Thermo Scientific). Deep Vent$_R$™ exo-DNA Polymerase was purchased from New England Biolabs (NEB). Synthesized oligonucleotides (primers) were purchased from Tech Drogon Limited. GelRed™ Nucleic Acid Gel Stain (10000× in water) was purchased from Biotium. Other chemicals, reagents and solvents were all purchased from Aldrich or Invitrogen. $^1$H and $^{13}$C NMR spectra were measured on a Bruker ARX 400 NMR spectrometer using $CDCl_3$ as solvent. High-resolution mass spectra (HRMS) were taken on a Finnigan TSQ 7000 triple quadrupole spectrometer in a MALDI-TOF mode. UV spectra were measured on a Milton Roy Spectronic 3000 Array spectrophotometer. Fluorescence (FL) spectra were recorded on a Perkin-Elmer LS 55 spectrofluorometer. FL quantum yields ($\Phi_F$) of amorphous powders of siloles were measured using C-701 Time-Resolved Spectrofluorometer with the integrating sphere as accessory.

1,2-bis[4-(isothiocyanatemethyl)phenyl]-1,2-diphenylethene (TPENCS) was synthesized according to Scheme 1 shown below.

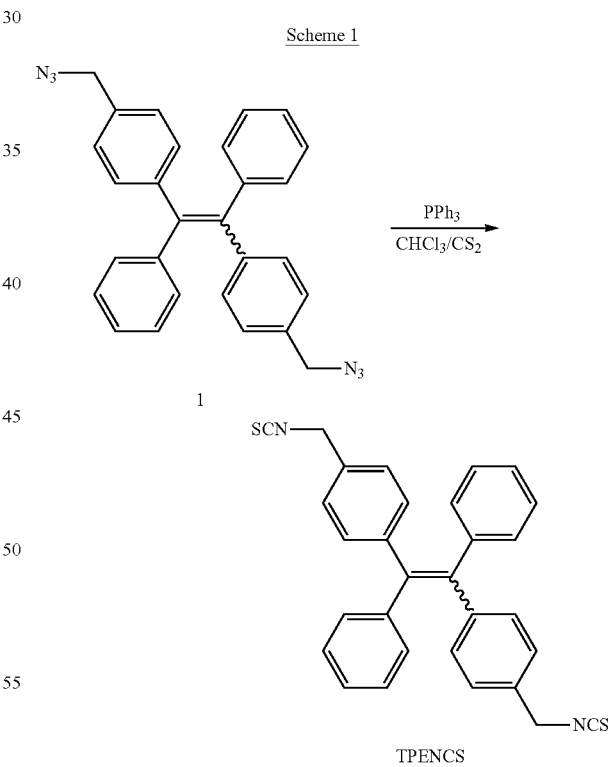

Triphenylphosphine (PPh$_3$; 131.1 mg, 0.5 mmol) was added to a solution of 1,2-bis[4-(azidomethyl)phenyl]-1,2-diphenylethene (1, Scheme 1) (110.5 mg, 0.25 mmol) and carbon disulfide (CS$_2$; 0.24 ml, 4.0 mmol) in chloroform (CHCl$_3$; 1.0 ml) at room temperature. The mixture was stirred for 1.5 h. After solvent evaporation under reduced pressure, the crude product was purified by a silica gel column using ethyl acetate/hexane (1:10 v/v) as eluent. A white powder of 1,2-bis[4-(isothiocyanatemethyl)phenyl]-1,2-diphenylethene (TPENCS) was obtained in 60% yield.

Characterization Data for TPENCS (Scheme 1): $^1$H NMR (400 MHz, CDCl$_3$), δ (ppm): 7.12-7.09 (m, 6H), 7.04-6.99 (m, 12H), 4.62-6.61 (m, 4H). $^{13}$C NMR (100 MHz, CDCl$_3$), δ (ppm): 143.7, 143.1, 140.6, 132.3, 132.2, 131.7, 131.2, 127.9, 127.7, 126.7, 126.2, 126.1, 48.4. HRMS (MALDI-TOF), m/e: 474.1454 ([M]$^+$, calcd 474.1224).

1-[4-bromophenyl]-1,2,2-triphenylethene (TPEMBR) was synthesized according to Scheme 2 shown below.

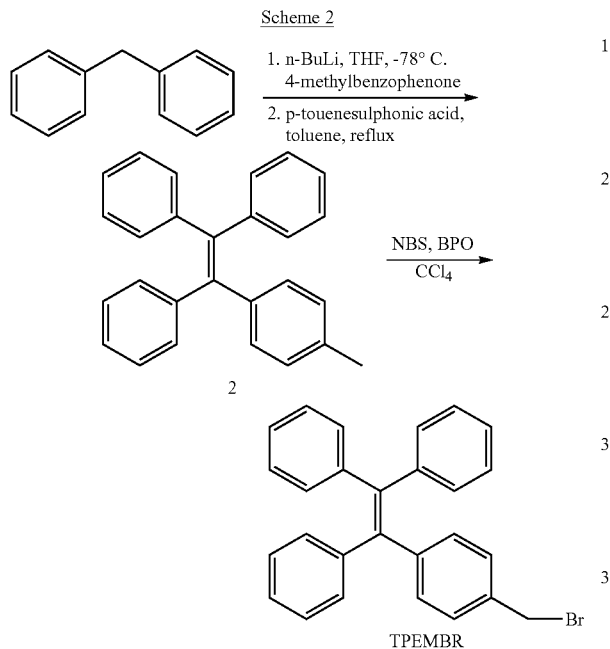

Scheme 2

4 mL of a 2.5 M solution of n-butyllithium in hexane (10 mM) was added to a solution of diphenylmethane (2.02 g, 12 mM) in dry THF (20 mL) in an acetone-dry ice bath at −78° C. under nitrogen atmosphere. The resulting orange-red solution was stirred for 30 min at that temperature. 4-methylbenzophenone (9 mM) was added to this solution and the reaction mixture was allowed to warm to room temperature with stirring for 6 hr. The reaction was quenched with the addition of an aqueous solution of ammonium chloride. The organic layer was extracted with dichloromethane (DCM), and the combined organic layers were washed with a saturated brine solution and dried over anhydrous MgSO$_4$. The solvent was evaporated, and the resulting crude alcohol was dissolved in about 80 mL of toluene in a 100 mL Schlenk flask fitted with a Dean-Stark trap. A catalytic amount of p-toluenesulphonic acid (342 mg, 1.8 mM) was added, and the mixture was refluxed for 3-4 h and cooled to room temperature. The toluene layer was washed with 10% aqueous NaHCO$_3$ solution, dried over anhydrous MgSO$_4$ and evaporated to afford the crude tetraphenylethene derivative 1-[4-methylphenyl]-1,2,2-triphenylethene (2, Scheme 2). The crude product was purified on a silica-gel column using hexane as eluent. A white powder of the tetraphenylethene derivative 1-[4-methylphenyl]-1,2,2-triphenylethene (2) was obtained in 93.6% yield. A catalytic amount of BPO was added to a mixture of the tetraphenylethene derivative 1-[4-methylphenyl]-1,2,2-triphenylethene (2) (1.8 g, 5.0 mM) and NBS (0.85 g, 5.0 mM) in CCl$_4$ at room temperature. The mixture was stirred and heated to reflux for 8 hr. After filtration and solvent evaporation, the product was purified by silica gel chromatography using DCM/hexane (1:4 v/v) as eluent. 1-[4-bromophenyl]-1,2,2-triphenylethene (TPEMBR) was isolated as pale yellow solid in 72%.

Characterization Data for TPEMBR (Scheme 2): $^1$H NMR (400 MHz, CDCl$_3$), δ (TMS, ppm): 7.07-7.13 (m, 11H), 6.98-7.05 (m, 8H), 4.41 (d, 2H). $^{13}$C NMR (CDCl3, 100 MHz) δ (ppm): 34.04, 126.75, 126.8, 126.93, 126.98, 127.97, 128.04, 128.14, 128.81, 131.67, 131.73, 132.06, 136.07, 140.59, 141.91, 143.80, 143.87, 143.92, 144.35. MS (MALDI-TOF), m/e: 426.1 ([M+2H]$^+$, calcd 426.1).

1,1-dimethyl-2,5-bis[4-(isothiocyanatemethyl)phenyl]-3,4-diphenylsilole (SITC) was synthesized according to Scheme 3 shown below.

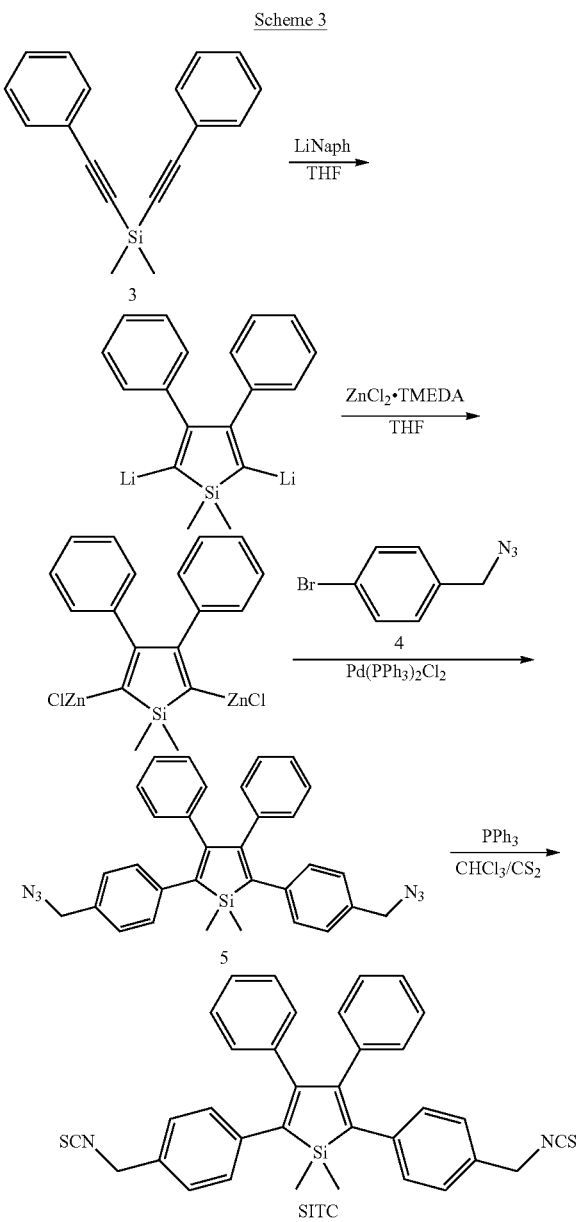

Scheme 3

4-bromobenzyl bromide (7.5 g, 30 mmol), sodium azide (7.8 g, 120 mmol), and 40 mL of DMSO were added into a flask equipped with a magnetic stirrer. After stirring at 70° C. for 12 h, the solution was poured into 150 mL of water and extracted with $CH_2Cl_2$. The crude product was purified by silica-gel chromatography to give a colorless viscous liquid 4-bromobenzylazide (4, Scheme 3) in 96.2% yield (6.12 g).

Characterization Data for 4 (Scheme 3): $^1H$ NMR ($CDCl_3$, 400 MHz), δ (TMS, ppm): 7.47 (d, J=8.2 Hz, 2H, Ar), 7.15 (d, J=8.2 Hz, 2H, Ar), 4.26 (s, 2H, $CH_2$). $^{13}C$ NMR ($CDCl_3$, 100 MHz), δ (TMS, ppm): 134.3, 131.8, 129.6, 122.1, 53.9. FIRMS (MALDI-TOF): m/z 210.9640 ($M^+$, calcd 210.9745).

A mixture of lithium (0.056 g, 8 mmol) and naphthalene (1.04 g, 8 mmol) in 8 mL of THF was stirred at room temperature under nitrogen for 3 h to form a deep dark green solution of LiNaph. The viscous solution was then added dropwise to a solution of dimethyl[bis(phenylethynyl)]silane (3, Scheme 3) (0.52 g, 2 mmol) in 5 mL of THF over 4 min at room temperature. After stirring for 1 h, the mixture was cooled to 0° C. and then diluted with 25 mL THF. A black suspension was formed upon addition of $ZnCl_2$.TMEDA (2 g, 8 mmol). After stirring for an additional hour at room temperature, a solution of 4-bromobenzylazide (4, Scheme 3) (0.89 g, 4.2 mmol) and $PdCl_2(PPh_3)_2$ (0.08 g, 0.1 mmol) in 25 mL of THF was added. The mixture was refluxed overnight. After cooling to room temperature, 100 mL of 1 M HCl solution was added and the mixture was extracted with DCM. The combined organic layer was washed with brine and water and then dried over magnesium sulfate. After solvent evaporation under reduced pressure, the residue was purified by a silica-gel column using hexane as eluent. The 1,1-dimethyl-2,5-bis[4-(azidomethyl)phenyl]-3,4-diphenylsilole (5, Scheme 3) was obtained as a yellow solid in 57.3% yield.

Characterization Data for 1,1-dimethyl-2,5-bis[4-(azidomethyl)phenyl]-3,4-diphenylsilole (5, Scheme 3): $^1H$ NMR (400 MHz, $CDCl_3$), δ (TMS, ppm): 7.06 (d, J=8.1 Hz, 4H, Ar), 7.01 (m, 6H, Ar), 6.92 (d, J=8.1 Hz, 4H, Ar), 6.78 (m, 4H, Ar), 4.24 (s, 4H, $CH_2$), 0.47 (s, 6H, $CH_3$). $^{13}C$ NMR (100 MHz, $CDCl_3$), δ (TMS, ppm): 154.3, 141.3, 139.9, 138.5, 132.4, 129.9, 129.1, 127.9, 127.5, 126.3, 54.6, −3.9. FIRMS (MALDI-TOF): m/z 524.2200 ($M^+$, calcd 524.2145).

$PPh_3$ (131.1 mg, 0.5 mmol) was added to a solution of 1,1-dimethyl-2,5-bis[4-(azidomethyl)phenyl]-3,4-diphenylsilole (5, Scheme 3) (131 mg, 0.25 mmol) and $CS_2$ (0.24 ml, 4.0 mmol) in $CHCl_3$ (1.0 ml) at room temperature. The mixture was stirred for 1.5 h. After solvent evaporation under reduced pressure, the crude product was purified by a silica-gel column using ethyl acetate/hexane (1:10 v/v) as eluent. The product 1,1-dimethyl-2,5-bis[4-(isothiocyanatemethyl)phenyl]-3,4-diphenylsilole (SITC, Scheme 3) was obtained as a yellow solid in 57.3% yield.

Characterization Data for SITC (Scheme 3): $^1H$ NMR (400 MHz, $CDCl_3$), δ (TMS, ppm): 7.04 (d, J=6.4 Hz, 4H, Ar), 7.00 (m, 6H, Ar), 6.93 (d, J=8.4 Hz, 4H, Ar), 6.79 (m, 4H, Ar), 4.62 (s, 4H, $CH_2$), 0.47 (s, 6H, $CH_3$). $^{13}C$ NMR (100 MHz, $CDCl_3$), δ (TMS, ppm): 154.5, 141.2, 139.9, 138.4, 131.2, 129.9, 129.2, 127.5, 126.5, 126.4, 48.4, −3.9. FIRMS (MALDI-TOF): m/z 556.1462 ($M^+$, calcd 556.1463).

Example 2

Preparation of SITC-dUTP

SITC (5 mM in DMSO, 25 μL) was added to a water solution of 5-(3-aminoallyl)-2'-deoxyuridine-5'triphosphate (aa-dUTP, 10 mM, 10 μL). The mixture was incubated at room temperature for 6 h with agitation and used directly without purification. HRMS (MALDI-TOF), m/z: 1077.2860 ($[M+2H]^+$, calcd 1077.1465).

The modification site of aa-dUTP is the C-5 position of the pyrimidine ring, which does not participate in the base-pair hydrogen bonding. To avoid cross-linking of aa-dUTPs by SITC which contains two isothiocyanate groups, a solution of SITC in DMSO was added into aa-dUTP solution with the amount of SITC equal to that of aa-dUTP.

Example 3

SDS-PAGE Gel Electrophoresis

The protein samples were treated with denaturing 4× sample buffer containing 62.5 mM Tris (pH 8.5), 20% (v/v) glycerol, 4% SDS (w/v), and 3% (w/v) DTT for 5 min at 85~95° C. in Protein Lobind Eppendorf cups. Serial dilutions of the proteins were labeled and loaded onto the gel lanes. Electrophoresis was carried out on self-cast polyacrylamide mini-gels (1 mm thick) using a discontinuous buffer system. The separation gel (pH 8.8) contained 12% polyacrylamide. The stacking gel (pH 6.8) contained 4% polyacrylamide. Both gels have an acrylamide/bis ratio of 37.5:1. The running buffer contained 25 mM Tris (pH 8.6), 192 mM glycine and 0.1% SDS (w/v) in water. All solutions were freshly prepared prior to use. SDS-PAGE was carried out on a vertical polyacrylamide gel system at a current of 15 mA until the protein bands reached the interface of the separating gel. Separation was performed at 100 V for two hours.

Fluorescence Prestaining with TPENCS

Fluorescence prestaining of proteins for SDS-PAGE gels was applied prior to the denaturation step. About 1 mg of the protein was dissolved in 1 mL of 0.1 M sodium bicarbonate buffer solution (15 μM). 10 μL of TPENCS DMSO stock solution (5 mM) was added to 100 μL protein solution. The pH was optimized to ~9 by adding 1 M sodium bicarbonate buffer. The reaction mixture was incubated for 2 h at 37° C. in an Eppendorf Thermomixer. Then, samples were cooled either to room temperature for instant use or frozen for eventual use.

Coomassie Brilliant Blue (CBB) Poststaining and Destaining 2.5 g of Coomassie blue R250 was dissolved in 1000 mL of 50% (v/v) methanol, 10% (v/v) acetic acid, and 40% (v/v) water with stirring as needed. The solution was filtered to remove any insoluble material. The final concentration of Coomassie blue R250 was 0.25% (w/v). After electrophoresis, the apparatus was disassembled and the gel was immerged into CBB solution. The gel was stained at room temperature overnight with gentle agitation. The Coomassie stain was removed by aspiration after staining. The gel was then immerged into the destaining solution composed of 50% (v/v) methanol, 10% (v/v) acetic acid, and 40% (v/v) water which allowed the gel to destain with gentle agitation. The destaining step was repeated several times, removing destaining solution at each change by aspiration. The destaining was continued until the protein bands were seen clearly without any background staining of the gel.

Fluorescent Poststaining and Destaining with TPENCS

The protocol of gel fluorescent poststaining with TPENCS was similar to that of the CBB poststaining. The only difference was that the composition of the staining solution was prepared by mixing 1 mL DMSO stock solution of TPENCS (5 mM) with 20 mL 10% SDS aqueous (w/v) solution, and the pH was optimized to ~9.0 by adding 1 M sodium bicarbonate buffer. The destaining solution was 10% SDS aqueous (w/v) solution. Similar to the destaining protocol of Coomassie brilliant blue, the gel was immersed into the 10% SDS aqueous (w/v) solution and destained with gentle agitation. The destaining solution was changed every two hours and the whole destaining process was finished within six hours.

Staining Effect of TPENCS

Figure 2:
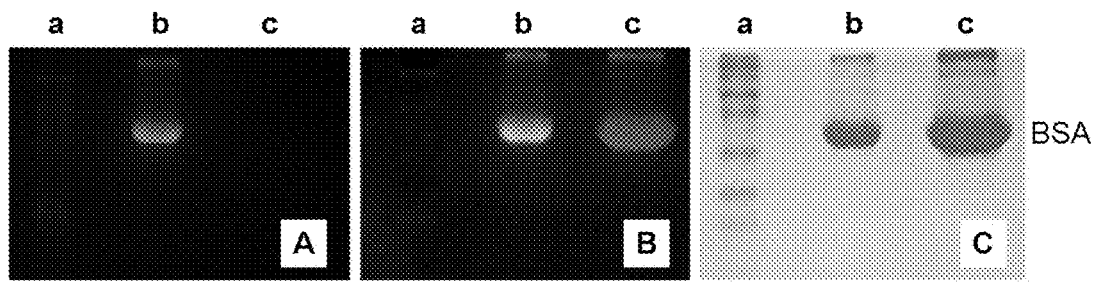

Since nearly all kinds of proteins have reactive amine groups (lysine residues) on their molecular chains, bovine serum albumin (BSA), a commonly used protein, was employed as a test sample to verify the staining effect of TPENCS. The prestained BSA was loaded onto the gel lane b and a pure BSA sample was loaded on lane c at the same time as a control. After electrophoresis, the gel fluorescent image was taken under UV excitation within the Gel Doc XR+ documentation system (FIG. 2a). As expected, the prestained sample in lane b was highly emissive just after the electrophoresis due to the presence of TPENCS chemically bound with BSA while the pure BSA sample in lane c was nonemissive. The gel was then introduced to the poststaining procedure and the fluorescent image was again obtained (FIG. 2b). The emission from the band in lane c after poststaining demonstrated the success of the reaction between TPENCS and BSA in the gel. Both emissive bands in the gel were shown to be BSA by CBB staining results (FIG. 2c).

These results showed that TPENCS reacted with the amine group of the proteins very efficiently via both prestaining and poststaining methods. The position of the BSA bands in lanes b and c is the same, indicating that TPENCS has no significant effect on protein migration rate.

Prestaining Sensitivity of TPENCS

Figure 3:
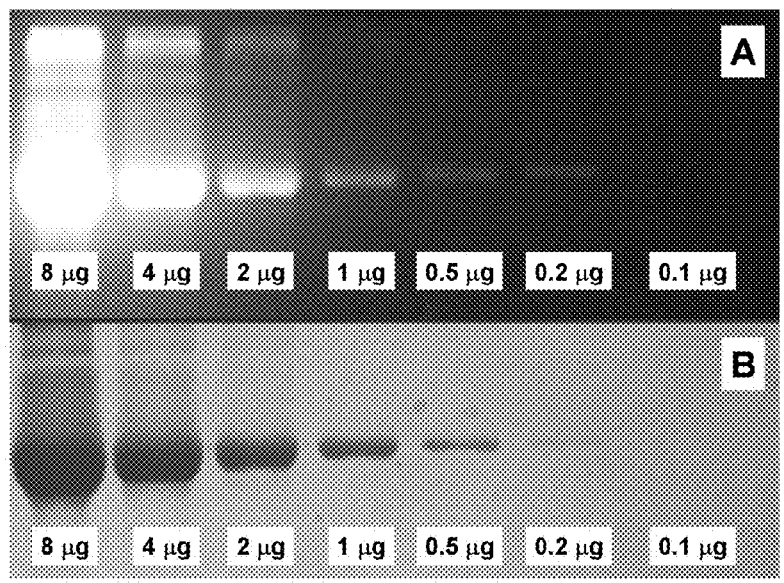
FIG. 3a shows an SDS-PAGE fluorescence image of TPENCS prestained BSA with various loaded amount of protein.
FIG. 3b shows an image of the gel of TPENCS prestained BSA with various loaded amount of protein restained with Coomassie R-250.

To evaluate the prestaining sensitivity of TPENCS, the entire prestaining and electrophoresis processes were repeated with a series of progressively diluted BSA samples. Under identical staining conditions, the emission of a band was directly proportional to the loaded amount of protein and thus decreased with the dilution of the protein samples (FIG. 3a). The CBB restaining of the same gel showed the same results as those from the compound TPENCS prestaining (FIG. 3b). Both TPENCS prestaining and CBB staining achieved a limit of detection (LOD) as low as 0.2 µg in this gel electrophoresis process. However, CBB staining was time consuming and had strong background with the gel image.

Comparison Between TPENCS Poststaining and CBB Staining

Figure 4:
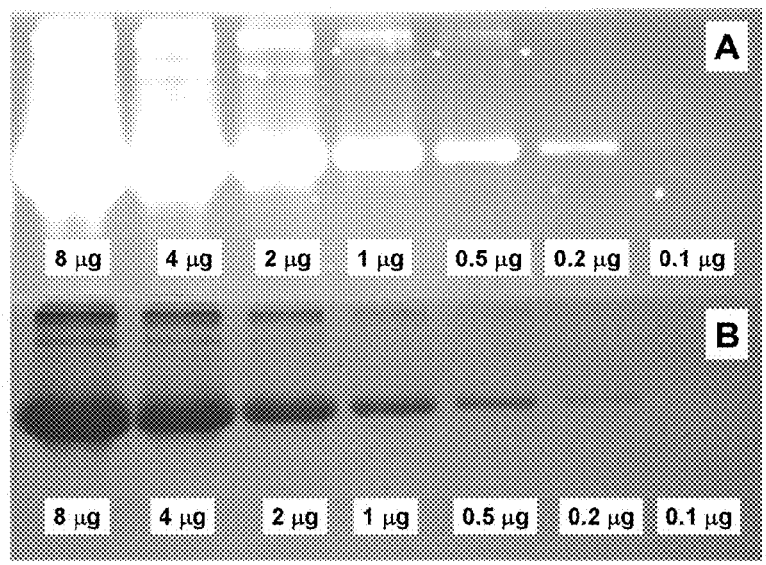
FIG. 4a shows an SDS-PAGE fluorescence image of TPENCS poststained BSA with various loaded amount of protein.
FIG. 4b shows an image of the gel of TPENCS poststained BSA with various loaded amount of protein restained with Coomassie R-250.

A comparison between TPENCS poststaining and CBB staining was carried out. The LOD was improved to 0.1 µg (FIG. 4a) via fluorescent poststaining due to the increase in the amount of TPENCS bound with the BSA through a longer labeling process while the LOD for CBB staining remained the same (FIG. 4b). This observation provides a means for improving the sensitivity of TPENCS via poststaining method with a longer reaction time.

Linearity of Response of Prestaining and Poststaining Methods

Figure 5:
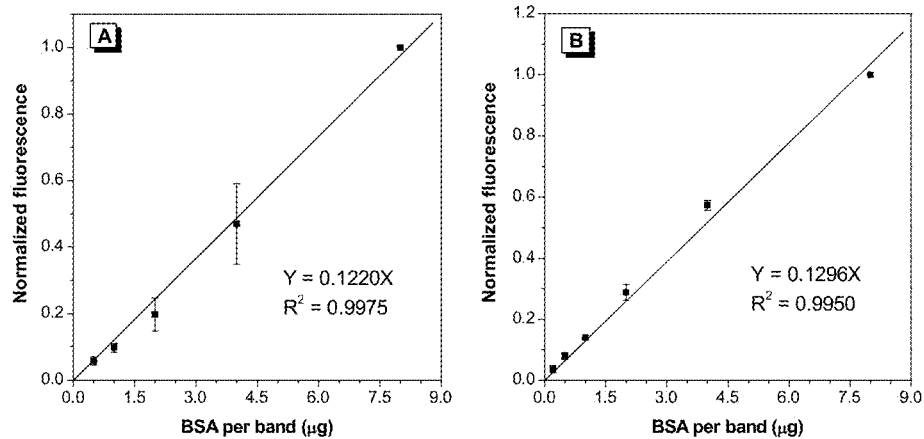
FIG. 5a shows a graph of normalized fluorescence versus the amount of TPENCS prestained BSA in the SDS-PAGE assay.
FIG. 5b shows a graph of normalized fluorescence versus the amount of TPENCS poststained BSA in the SDS-PAGE assay.

The linearity of response was investigated for both the prestaining and poststaining methods with TPENCS. Fluorescence intensities were obtained for a series of progressively diluted BSA samples with three independent experiments for each sample. The bands with the highest amount of BSA were used as the reference and a plot of the normalized fluorescence versus the amount of protein was obtained (FIGS. 5a and 5b). Excellent linear responses with good correlation coefficients were achieved from 0.5 to 8 µg for prestaining and 0.2 to 8 µg for poststaining. The results enabled the detection and quantification of proteins in PAGE gel by comparing the fluorescence intensities between a sample and a standard in the same gel.

Example 4

Detection of Proteins

All stained gels were imaged with the Gel Doc XR+ documentation system (Bio-Rad). The images were analyzed by Quantity One gel image analysis software (Bio-Rad). The trace quantity, which represented the intensity of each pixel multiplied by the band-area ($mm^2$), was plotted versus the protein amount.

Comparison of Protein Labeling of FITC and TPENCS

Figure 6:
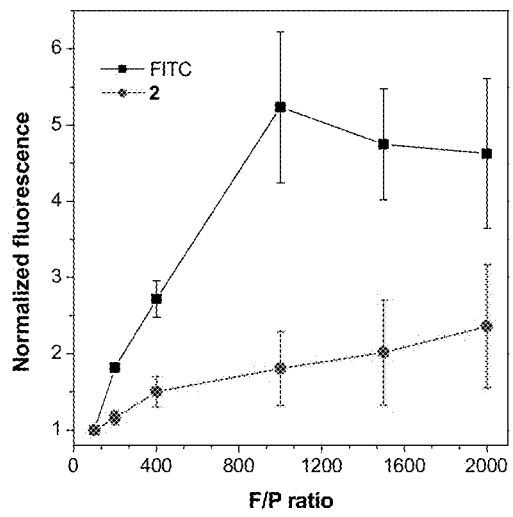
FIG. 6 shows a graph of normalized fluorescence versus F/P ratio in the SDS-PAGE assay via the prestaining method.

A comparison of the protein labeling effect in gel between traditional self-quenching dyes and the novel AIE dye was demonstrated by using FITC and TPENCS via the prestaining method. An equal amount of BSA was labeled with a series of concentrations of FITC and of TPENCS. After the electrophoresis, the gel fluorescent image was taken under UV excitation. Fluorescence intensities were obtained from three independent experiments. Fluorescence intensities normalized with the sample with the lowest dye concentration were plotted versus the F/P ratio (FIG. 6). Self-quenching effect was observed when 1000 times of FITC was used to label protein samples, while the fluorescence intensities of the TPENCS labeled protein samples kept increasing. This self-quenching effect is inevitable for aggregation-caused quenching dyes such as FITC and hence limits the application of such dyes on quantification of proteins on gel.

SDS-PAGE

Figure 7:
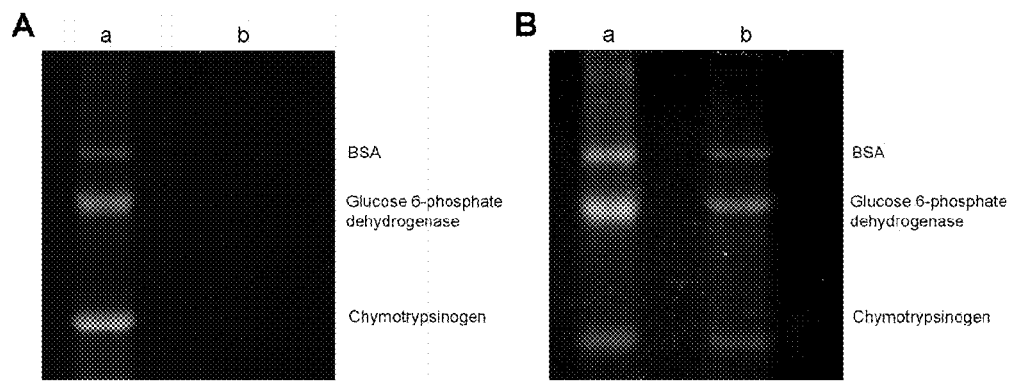
FIG. 7a shows an SDS-PAGE fluorescence image of the TPENCS prestained sample with various proteins (lane a) and pure proteins (lane b).
FIG. 7b shows an SDS-PAGE fluorescence image of the TPENCS poststained sample.

To mimic a real SDS-PAGE staining process, three proteins with different molecular weights (BSA, 66 KD, Glucose 6-phosphate dehydrogenase, 57 KD and Chymotrypsinogen, 25 KD) were mixed together and equally divided into two portions. One portion was prestained and loaded into lane a of the gel, while the other portion without any staining was loaded into lane b. The fluorescent image of the TPENCS prestained sample was taken right after electrophoresis (FIG. 7a). Three fluorescent bands which represent the three different proteins were observed in lane a. The sample in lane b was not prestained and thus invisible. Poststaining method was then applied to the same gel, followed by fluorescence imaging. Fluorescent bands observed in lane b after poststaining were the same as the prestained bands in lane a (FIG. 7b).

From these results, it was confirmed that different proteins could be labeled by both the prestaining and poststaining methods and all the emissive bands were located at the same position. The AIE polyene TPENCS with two reactive groups did not crosslink different proteins because the steric effect of protein molecules inhibited the crosslinking of proteins during prestaining. It can also be seen that the image from prestaining possessed a lower signal-to-noise ratio than that from poststaining.

Protein Transfer

Figure 8:
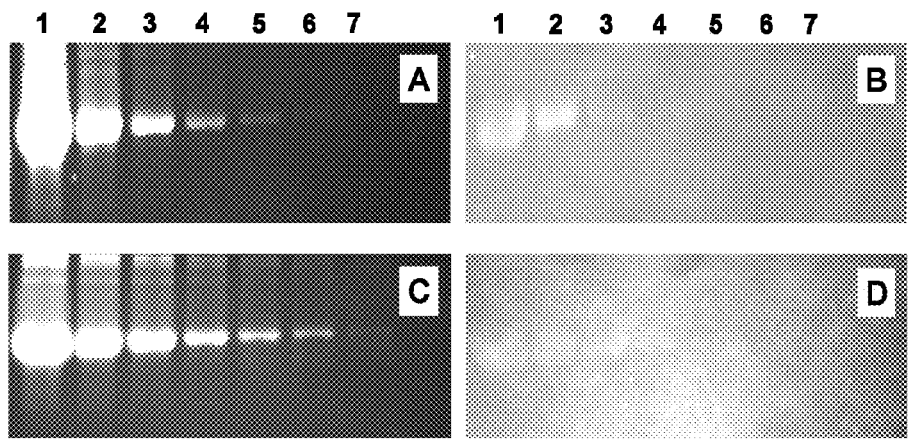
FIG. 8a shows an SDS-PAGE fluorescence image of BSA prestained with TPENCS.
FIG. 8b shows an image of TPENCS prestained BSA transferred onto nitrocellulose membrane.
FIG. 8c shows an SDS-PAGE fluorescence image of BSA poststained with TPENCS.
FIG. 8d shows an image of TPENCS poststained BSA transferred onto nitrocellulose membrane.

Without fixing the proteins on gel, the transfer of the TPENCS labeled proteins from gel to nitrocellulose membranes can be achieved for both prestaining and poststaining methods. The fluorescent images of the membranes were taken immediately after transfer (FIGS. 8b and 8d) and compared with the images of the gels (FIGS. 8a and 8c). The semitransparent nitrocellulose membrane weakened the excitation UV light from its backside and therefore the sensitivities on the other side were much lower than that on the gels. The LODs on nitrocellulose membrane were 2 μg for prestaining (FIG. 8b) and 1 μg for poststaining (FIG. 8d). The success of protein transfer for both prestaining and poststaining methods offers the possibility of further investigation of labeled proteins.

Example 5

General Fluorescent Labeling of Cys Containing Protein 2.5 μL Tris-HCl (1 M), 2.5 μL TCEP (20 mM), 5 μL BSA (1 mg/mL, 15 μM), and 30 μL urea (8 M in water) was added to a 1.5 mL Eppendorf tube and mixed well. The mixture was incubated at room temperature for 30 min to pre-reduce the disulfide bonds with TCEP. Then, 10 μL of the TPEMBR DMSO stock solution (2.5 mM 5×) was added to the system and made the final volume 50 μL. The reaction mixture was incubated for 3 hours at 50° C. in an Eppendorf Thermomixer. Then, samples were cooled either to room temperature for instant use or frozen for eventual use.

Figure 11:
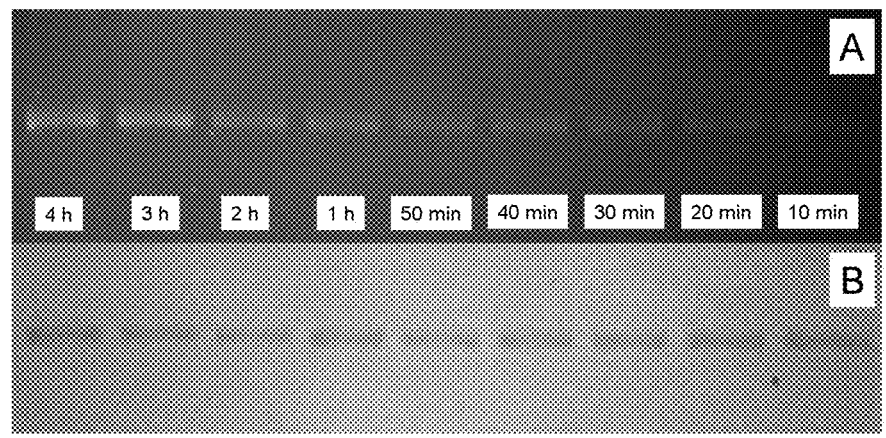
FIG. 11a shows an SDS-PAGE fluorescence image of TPEMBR stained BSA with various labeling times.
FIG. 11b shows an image of the gel of TPEMBR stained BSA with various labeling times restained with Coomassie R-250.

In order to ensure that the Cys residues were sufficiently labeled with TPEMBR, a longer reaction time (usually overnight) at or below room temperature was required. Alternatively, the reaction time could be reduced if labeling was carried out at 50° C. To verify the time-dependence of labeling efficiency, bovine serum albumin (BSA) samples were labeled with TPEMBR for different times ranging from 10 min to 4 h and analyzed by SDS-PAGE. The fluorescence intensity of the labeled BSA increased as the reaction time was extended. The maximum intensity under specific labeling conditions was observed after 3 h and remained unchanged even with an additional 1 h of reaction time (FIGS. 11a and 11b). Based on this result, reaction time should be controlled within 4 h to avoid any undesired nonspecific labeling. The time-dependent labeling effect provides a way to determine the desirable DOL according to different applications by simply controlling the labeling time. Meanwhile, a lower temperature labeling process with a longer reaction time could be a better choice to obtain fluorescent proteins while maintaining their native structures.

BSA samples were subjected to labeling with different dye concentrations. The SDS-PAGE fluorescence intensity of labeled BSA increased with increasing dye concentration. The maximum intensity was reached at a dye concentration of 0.5 mM or above (FIG. 12a). Further increasing the dye concentration could give higher fluorescence intensity due to nonspecific labeling. Clearly, the DOL of protein samples can be controlled by varying the dye concentration. It is notable that the migrating rates of the BSA labeled by TPEMBR with different concentrations were comparable with that of the pure denatured BSA sample (FIG. 12b) on the same SDS-PAGE gel. This indicates that labeling Cys residues of the protein with TPEMBR had little effect on its molecular mass.

Figure 13:
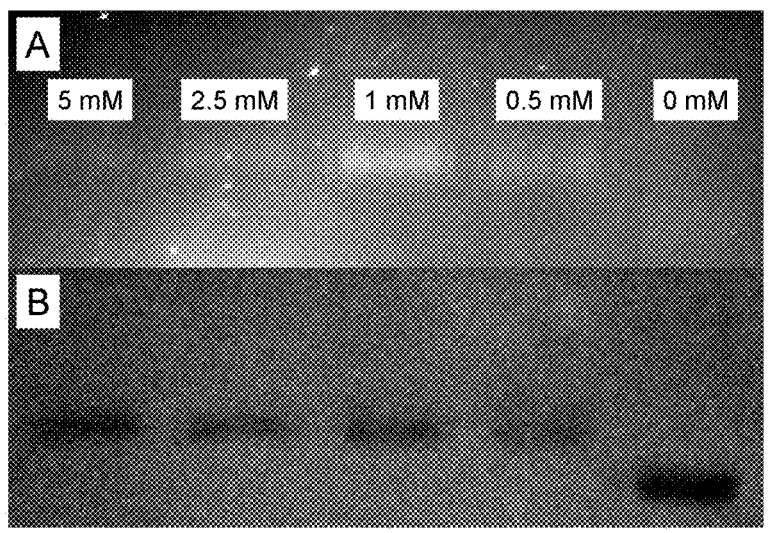
FIG. 13a shows an SDS-PAGE fluorescence image of TPEMBR stained BSA with various concentrations of TCEP.
FIG. 13b shows an image of the gel of TPEMBR stained BSA with various concentrations of TCEP restained with Coomassie R-250.

The thiol groups of proteins usually exist as a disulfide bond that needs to be completely reduced to enable effective labeling using reducing reagents such as DTT, β-mercaptoethanol or TCEP. DTT and β-mercaptoethanol are reagents traditionally used for the reduction of disulfide bonds. However, they could react with the thiol-reactive fluorescent dyes and need to be removed prior to fluorescent labeling. Phosphines such as TCEP usually have a much lower reactivity toward thiol-reactive compounds and do not need to be removed prior to the alkylating reaction. Hence, in order to obtain the desired labeling effect, we set out to explore the optimal concentration of TCEP in the labeling reaction. From the results shown in FIG. 5a, among all the BSA samples reduced with various concentrations of TCEP, reduction of BSA with 1 mM TCEP produced the highest fluorescence intensity after labeling with TPEMBR. Lower concentrations of TCEP only gave incomplete reduction of disulfide bonds; higher concentrations induced the undesired reaction of TPEMBR and TCEP. As a control experiment, the sample without treating with TCEP prior to labeling showed no emission at all (FIG. 13a). After restaining the gel with coomassie brilliant blue (CBB), it was observed that this sample without treatment with any reducing reagent before SDS-PAGE separation showed a higher migration rate on gel because it still kept the native folding structure stabilized by disulfide bonds (FIG. 13b).

Figure 14:
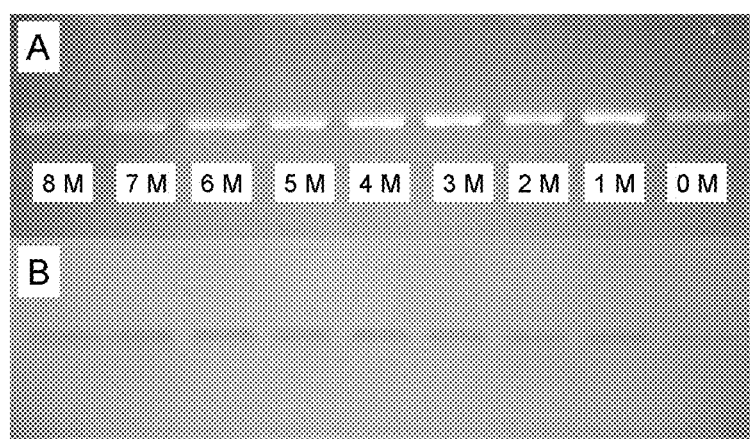
FIG. 14a shows an SDS-PAGE fluorescence image of TPEMBR stained BSA with various concentrations of urea.
FIG. 14b shows an image of the gel of TPEMBR stained BSA with various concentrations of urea restained with Coomassie R-250.

Urea can completely denature the proteins for effectively labeling and protein quantification. The concentration of urea commonly used for protein denaturation is 8 M. However, a lower concentration could eliminate desalting process before further applying the fluorescent labeling product. Protein samples were labeled with various concentrations of urea at 50° C. for 3 h with agitation. TPEMBR labeled BSA samples possessed the same fluorescence intensities when treated with varying concentrations of urea before labeling (FIGS. 14a and 14b). Thus, BSA could be denatured completely without any denaturants under the conditions stated above.

Figure 15:
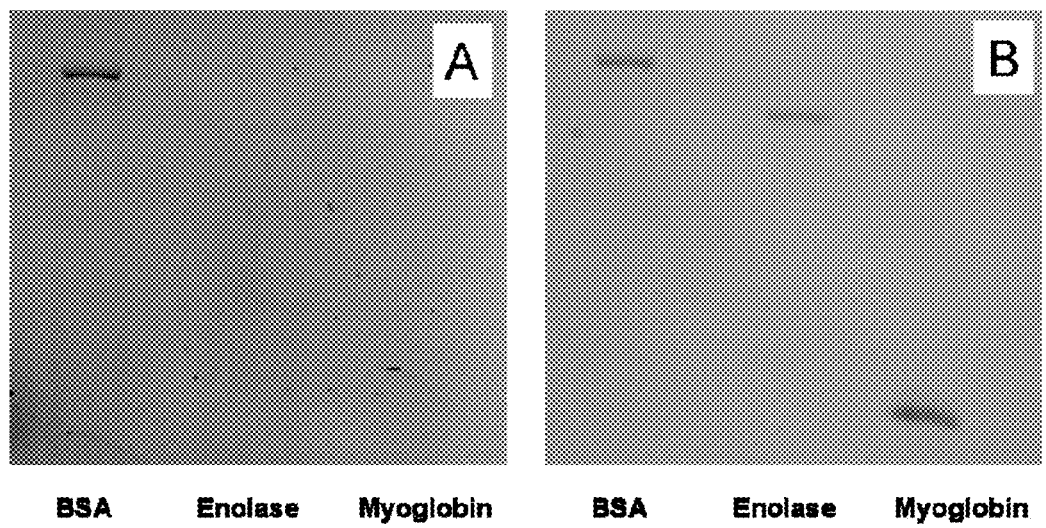
FIG. 15a shows an SDS-PAGE fluorescence image of TPEMBR stained protein samples with various contents of Cys.
FIG. 15b shows an image of the gel of TPEMBR stained protein samples with various contents of Cys restained with Coomassie R-250.

Specific labeling of Cys residues by TPEMBR was examined through the labeling of proteins with different Cys contents. BSA (35 Cys), yeast enolase (single Cys) and horse myoglobin (0 Cys) were labeled with 0.5 mM of TPEMBR, respectively. The corresponding fluorescent products were analyzed on gel. BSA with 35 Cys residues displayed a much higher emission than yeast enolase, which has only one Cys residue. Horse myoglobin, a protein without any Cys residue in its structure, showed no fluorescence at all (FIG. 15a). The results further confirmed the specificity of TPEMBR to Cys residue when the working concentration of 0.5 mM was used. The results from CBB staining showed that the three proteins had similar loading on the gel (FIG. 15b).

Figure 16:
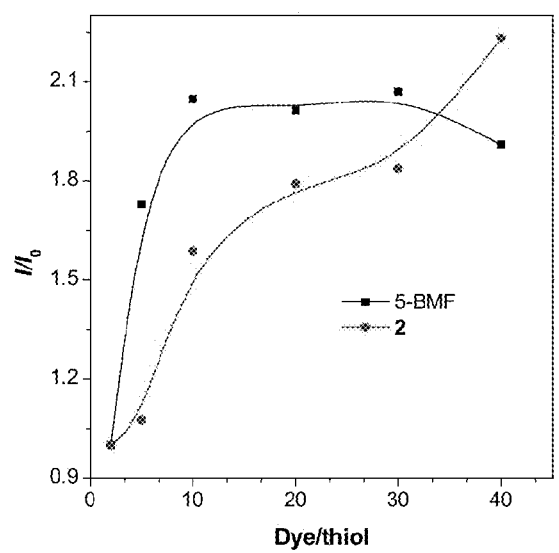
FIG. 16 illustrates the normalized fluorescence versus the dye/thiol ratio in the SDS-PAGE assay.

The comparison of protein labeling effect between self-quenching dyes and the novel AIE dyes was demonstrated by using 5-BMF and TPEMBR. BSA was labeled by each dye with a series of varying dye/thiol ratios. After the electrophoresis, the gel fluorescent image was taken under UV excitation and the fluorescence intensity was obtained from three independent experiments. Fluorescence intensities normalized with the sample with the lowest dye concentration are plotted versus the dye/thiol ratio (FIG. 16). Self-quenching effect was observed when 30 times of 5-BMF was used to label the Cys residues, while the fluorescence intensity of TPEMBR labeled protein samples kept on increasing. This self-quenching effect is inevitable for self-quenching dyes such as 5-BMF and limits these dyes' application on quantification of proteins. In contrast, detection and quantification of proteins with high contents of Cys can be easily achieved by using AIE active molecules such as TPEMBR.

Example 6

Labeling of DNA by Nick-Translation

General nick-translation process was carried out as follows: DNase I (1 unit/mL) was first diluted to 1/150 with 1×DNA polymerase I reaction buffer (10× from Fermentas) containing 0.05 mg/mL BSA and kept on ice. 2 µg of DNA template on ice was mixed with 1 µL of d A/G/CTP mixture (10 mM for each of them), 3.5 µL of SITC conjugated dUTP mixture (containing 1 µL of 10 mM conjugated dUTP), 10 µL of 10×DNA polymerase I reaction buffer (Fermentas), 10 µL of diluted DNase I and 4 µL of DNA polymerase I (10 units/µL), and then adequate water was added to make a final volume of 100 µL. The reaction mixture was incubated at 15° C. for 2 h and then purified by GeneJET™ PCR Purification Kit.

Labeling of DNA by Random Priming

General random priming process was carried out as follows: 2 µg of DNA template was denatured at 95° C. for 5 minutes and immediately cooled on ice. The denatured DNA template on ice was mixed with 1 µL of d A/G/CTP mixture (10 mM for each of them), 3.5 µL of SITC conjugated dUTP mixture (containing 1 µL of 10 mM conjugated dUTP), 10 µL of 10× random priming reaction buffer (Fermentas), 25 µL of random hexamer primer (0.2 µg/µL), 2 µL of Klenow fragment exo- (5 units/µL), and then adequate water was added to make a final volume of 100 µL. The reaction mixture was incubated at 37° C. for 4 h and then purified by GeneJET™ PCR Purification Kit.

A PCR product of plasmid DNA containing 1061 bp was used as template (SEQ ID NO. 1) for both nick translation and random priming. The PCR produce of plasmid DNA containing 1061 bp has the following sequence (SEQ ID NO. 1):

5'-GGGCCCCTGCAGGCTAAGCTAAGTTAACTGAGCTCTACTCGAGAAC

AAGGACGTCAACAGCTTCGACTTGGACGAACAAGATTTCGCTGACATTG

CCAAGTTGGACATCAACTTGAGATTCAACGACCCATGGGACTGGGACAA

GATTCCTATCTTCGTCTAAAAGCTTGCGAATTTCTTATGATTTATGATT

TTTATTATTAAATAAGTTATAAAAAAAATAAGTGTATACAAATTTTAAA

-continued
GTGACTCTTAGGTTTTAAAACGAAAATTCTTATTCTTGAGTAACTCTTT

CCTGTAGGTCAGGTTGCTTTCTCAGGTATAGCATGAGGTCGCTCTTATT

GACCACACCTCTACCGGCATGCCGAGCAAATGCCTGCAAATCGCTCCCC

ATTTCACCCAATTGTAGATATGCTAACTCCAGCAATGAGTTGATGAATC

GTCGTGTGTATTTTATGTCCTCAGAGGACAACACCTGTTGTAATCGTTC

TTTCCACACCCGACGCTTTTCAATTCATCTTTTTTTTTTTTGTTCTTTT

TTTTTGATTCCGGTTTCTTGAAATTTTTTTGATTCGGTAATCTCCGAGC

AGAAGGAAGAACGAAGGAAGGAGCACAGACTTAGATTGGTATATATACG

CATATGTGGTGTTGAAGAAACATGAAATTGCCCAGTATTCTTAACCCAA

CTGCACAGAACAAAAACATGCAGGAAACGAAGATAAATCATGTCGAAAG

CTACATATAAGGAACGTGCTGCTACTCATCCTAGTCCTGTTGCTGCCAA

GCTATTTAATATCATGCACGAAAAGCAAACAAACTTGTGTGCTTCATTG

GATGTTCGTACCACCAAGGAATTACTGGAGTTAGTTGAAGCATTAGGTC

CCAAAATTTGTTTACTAAAAACACATGTGGATATCTTGACTGATTTTTC

CATGGAGGGCACAGTTAAGCCGCTAAAGGCATTATCCGCCAAGTACAAT

TTTTTACTCTTCGAAGACAGAAAATTTGCTGACATTGGTAATACAGTCA

AATTGCAGTACTCTGCGACTAGTGAATTCGGGCCC-3'

Figure 18:
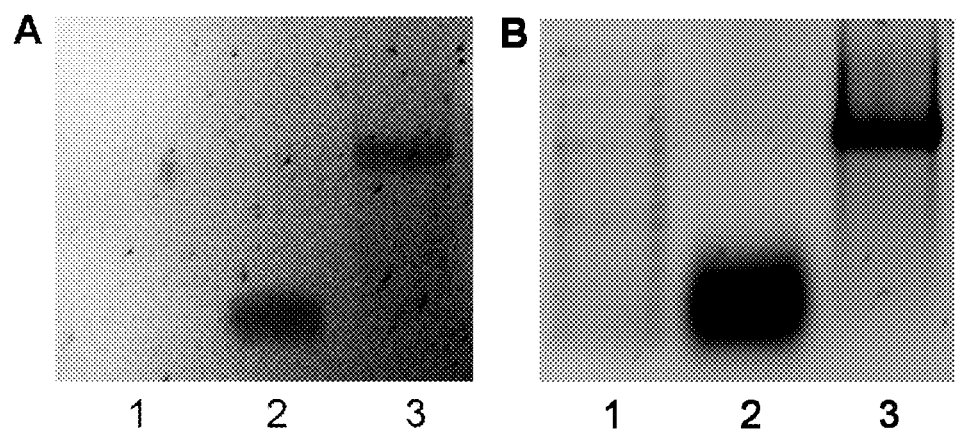
FIG. 18a shows a fluorescence image of SITC labeled DNA prepared through nick translation and random priming.
FIG. 18b shows a fluorescence image of the gel of SITC labeled DNA prepared through nick translation and random priming restained with GelRed.

Nick translation of this template was employed using DNase I and DNA polymerase I to prepare a pool of labeled DNA fragments (FIG. 18a, lane 2). On the other hand, degenerate oligonucleotides (e.g., random hexamer primer) were used together with DNA polymerase in random priming to synthesize uniformly labeled DNA strands (FIG. 18a, lane 3). The labeled double-stranded DNA (dsDNA) products were confirmed by GelRed poststaining (FIG. 18b). According to the results shown in FIGS. 2a and 2b, SITC labeled DNA products prepared by nick translation had a broad band with the bp number in the range of ~100 to ~300, while the random priming fluorescent products appeared as a uniform band of about 1k bp.

The 1061 bp template DNA was a PCR product of plasmid DNA. dTTP was replaced with increasing amount of SITC-dUTP. DOL of labeled DNA (number of dyes per 100 bases) were calculated from UV absorption base on Beer-Lambert law. The calculated molar extinction coefficient ($\epsilon$) of SITC is 10277 cm$^{-1}$M$^{-1}$ and its correction factor (CF) is 2.08. Table 1 shows the DOL of the fluorescent DNA prepared by nick translation and random priming using an increasing amount of SITC-dUTP. The DOL values of all the SITC labeled products are comparable to the results of DNA products labeled with traditional fluorescent dyes.

TABLE 1

| | | | |
|---|---|---|---|
| dTTP (µM) | 50 | 30 | 0 |
| SITC-dUTP (µM) | 50 | 70 | 100 |
| DOL of nick translation (number of dyes/100 bases) | 2.57 ± 0.61 | 4.01 ± 1.13 | 5.00 ± 1.19 |
| DOL of random priming (number of dyes/100 bases) | 2.64 ± 0.81 | 3.47 ± 0.70 | 3.52 ± 1.65 |

Example 7

Labeling of DNA by PCR

PCR reactions were carried out in a total of 100 µL mix containing 10 µL of 10× Long PCR buffer with 15 mM MgCl$_2$ (for Long PCR Enzyme Mix, Fermentas) or 10× Thermopol reaction buffer (for Deep Vent$_R$ exo-DNA Polymerase, NEB), 2 ng of the template DNA, 0.2 µM of primers, 2 units of Long PCR Enzyme Mix or Deep Vent$_R$™ exo-DNA Polymerase, and 0.2 mM of each of the dNTPs. In the control reaction, 0.2 mM of all the four normal dNTPs and no SITC-dUTP was used. In other cases, dTTP was substituted with different amounts of SITC-dUTP. PCR was performed in Veriti$^R$ 96-Well Thermal Cycler (Applied Biosystems). After an initial denaturation at 94° C. for 4 min, 35 cycles of PCR were carried out with denaturation at 94° C. for 0.5 min, annealing at 55° C.-58° C. (primer T$_m$-dependent) for 1 min and extension at 68° C. (Long PCR Enzyme Mix) or 72° C. (Deep Vent$_R$ exo-DNA Polymerase) for 1.5 min. After a 10 min final extension, the labeled DNA products were purified using GeneJET™ PCR Purification Kit. The DNA products were in 100 µL sterile water for spectroscopic measurement.

Agarose Gel Electrophoresis

The DNA samples with equal volumes were mixed with 6×DNA loading dye and analyzed on 1.5% agarose gel. The running buffer contained 40 mM Tris acetate and 1 mM EDTA in water. All solutions were freshly prepared prior to use. Gel electrophoresis was carried out on a Thermo Scientific horizontal Owl BIA EasyCast Mini Gel system. Separation was performed at 100 V for 30 min. The gels were either prestained with 1× GelRed (10000× in water from Biotium) or poststained with 50 mL 3× GelRed water solution.

Detection of dsDNA

All stained gels were imaged with the Gel Doc XR+ documentation system (Bio-Rad). The images were analyzed by Quantity One gel image analysis software (Bio-Rad).

Polymerase chain reaction (PCR) has many advantages over other enzymatic incorporation methods in preparing fluorescent DNA. Through the PCR method, simultaneous amplification and labeling of a specific DNA or a specific region of a DNA can be achieved. Thermophilic Deep Vent$_R$ exo-DNA polymerase (New England Biolabs) with high efficiency in incorporation of modified dNTPs to DNA was utilized to prepare SITC labeled DNA. Plasmid DNA with bp numbers of 94, 204, 304 (SEQ ID Nos. 2, 4, and 6, respectively) were selected as templates to prepare SITC labeled DNA products. SEQ ID NOs. 3, 5, and 7 are the corresponding primers. The templates and primers have the following sequences:

SEQ ID NO. 2:
5'-TCGAGAACAAGGACGTCAACAGCTTCGACTTGGACGAACAA

GATTTCGCTGACATTGCCAAGTTGGACATCAACTTGAGATTC

AACGACCCATG-3'

SEQ ID NO. 3:
5'-TCGAGAACAAGGACGTCAACA-3'

SEQ ID NO. 4:
5'-CACAGAACAAAAACATGCAGGAAACGAAGATAAATCATGT

CGAAAGCTACATATAAGGAACGTGCTGCTACTCATCCTAG

TCCTGTTGCTGCCAAGCTATTTAATATCATGCACGAAAAG

CAAACAAACTTGTGTGCTTCATTGGATGTTCGTACCACCA

AGGAATTACTGGAGTTAGTTGAAGCATTAGGTCCCAAAATTTGT-3'

SEQ ID NO. 5:
5'-CACAGAACAAAAACATGCAGG-3'

SEQ ID NO. 6:
5'-TCGAGAACAAGGACGTCAACAGCTTCGACTTGGACGAACAA

GATTTCGCTGACATTGCCAAGTTGGACATCAACTTGAGATTCAA

CGACCCATGGGACTGGGACAAGATTCCTATCTTCGTCTAAAAGCT

TGCGAATTTCTTATGATTTATGATTTTTATTATTAAATAAGTTATA

AAAAAAATAAGTGTATACAAATTTTAAAGTGACTCTTAGGTTTT

AAAACGAAAATTCTTATTCTTGAGTAACTCTTTCCTGTAGGTCAG

GTTGCTTTCTCAGGTATAGCATGAGGTCGCTCTTATTGA-3'

SEQ ID NO. 7:
5'-TCGAGAACAAGGACGTCAACA-3'

Figure 19:
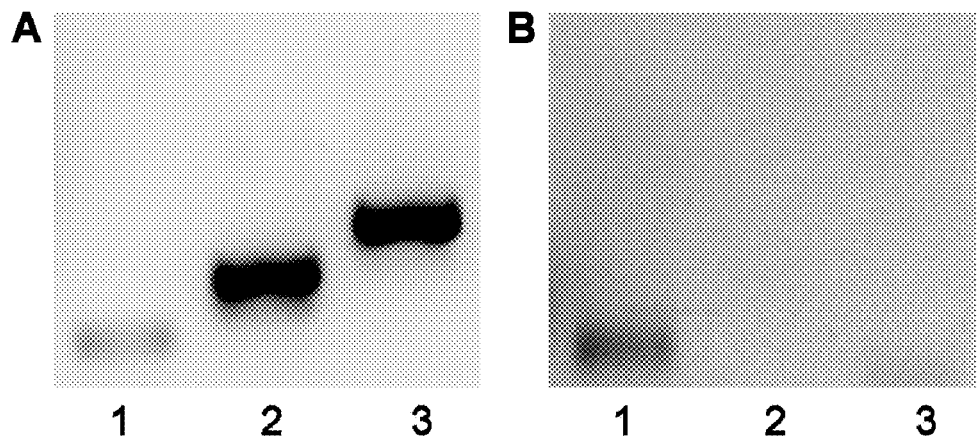
FIG. 19a shows a fluorescence image of DNA fragments prepared by PCR method with Long PCR Enzyme Mix and unlabeled dNTPs. Lanes 1-3 represent the DNA fragments with the base pair numbers of 94, 204 and 304.
FIG. 19b shows a fluorescence image of DNA fragments prepared by Deep Vent$_R$™ (exo-) DNA polymerase and SITC-dUTP. Lanes 1-3 represent the DNA fragments with the base pair numbers of 94, 204 and 304.

The results confirmed the successful amplifications of these three templates through normal PCR (FIG. 19a). On the other hand, preparation of SITC labeled DNA products were conducted by using Deep Vent$_R$ exo-DNA polymerase and SITC-dUTP. Only the template with 94 bp could be replicated during this process (FIG. 19b). As mentioned above, modified nucleoside triphosphates are incorporated less efficiently than the natural ones. It is suggested that PCR method could work efficiently only with the templates of ~100 bp or even shorter ones.

Figure 20:
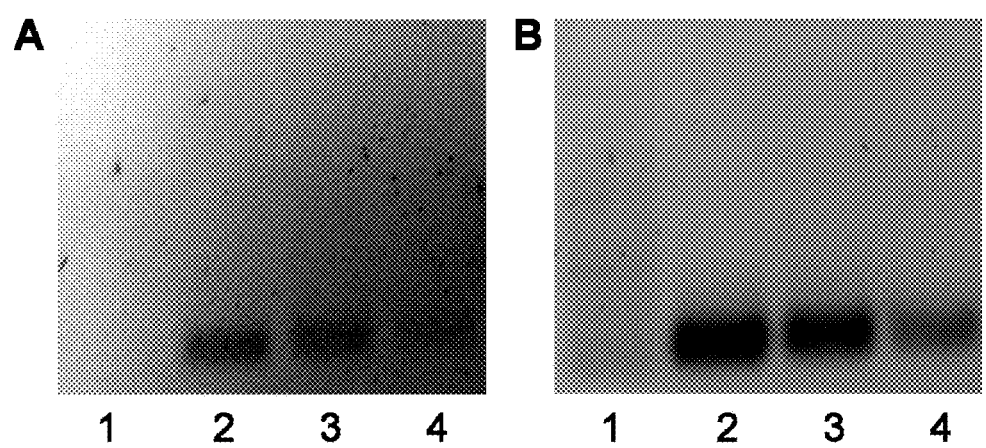
FIG. 20a shows a fluorescence image of SITC labeled DNA with various sequences prepared through PCR.
FIG. 20b shows a fluorescence image of the gel of SITC labeled DNA with various sequences prepared through PCR restained with GelRed.

Three SITC labeled DNA products with similar bp numbers of ~100 but different sequences were obtained through PCR with corresponding templates (SEQ ID NOs. 2, 8, and 10; FIG. 20a). SEQ ID NOs. 3, 9, and 11 are the corresponding primers. SEQ ID NOs. 8, 9, 10, and 11 have the following sequences:

SEQ ID NO. 8:
5'-CACAGAACAAAAACATGCAGGAAACGAAGATAAATCATGTCGA

AAGCTACATATAAGGAACGTGCTGCTACTCATCCTAGTCCTGTTG

CTGCCA-3'

SEQ ID NO. 9:
5'-CACAGAACAAAAACATGCAGG-3'

SEQ ID NO. 10:
5'-GTTAAGCCGCTAAAGGCATTATCCGCCAAGTACAATTTTTTACT

CTTCGAAGACAGAAAATTTGCTGACATTGGTAATACAGTCAAATT

GCAGTACTCTGCGA-3'

SEQ ID NO. 11:
5'-GTTAAGCCGCTAAAGGCATT-3'

The products were also confirmed to be dsDNA by GelRed poststaining (FIG. 20b). This result implied that the incorporation of SITC-dUTP through PCR with Deep Vent$_R$ exo-DNA polymerase can be achieved successfully with various DNA sequences.

A 103 bp DNA template (SEQ ID NO. 12) replicated from a region of a plasmid DNA was chosen for testing the effect of the relative amount of SITC-dUTP on the PCR products' fluorescence. SEQ ID NO. 13 is the corresponding primer. SEQ ID NOs. 12 and 13 have the following sequence:

SEQ ID NO. 12:
5'-CAGGAAACAGCTATGACCATGATTACGAATTCGAGCTCGGTACC

CGGGGATCCTCTAGAGTCGACCTGCAGGCATGCAAGCTTGGCACTG

GCCGTCGTTTTAC-3'

SEQ ID NO. 13:
5'-CAGGAAACAGCTATGAC-3'

This template had the highest yield of amplification through PCR with Deep Vent$_R$ exo-DNA polymerase and SITC-dUTP in our study. dTTP and SITC-dUTP with a total concentration of 200 μM were added into the 100 μL PCR system. The UV absorption and PL spectrum of the fluorescent products was obtained and the DOL values of the products prepared under various SITC-dUTP/dTTP ratios were calculated (Table 2). The highest DOL value we got was nearly 10 times than that was ever reported. There were 47 dTTP on the dsDNA template and 3 dTTP on the primers, so the number of dTTP which could be replaced by SITC-dUTP was 44. The theoretical DOL could be calculated accordingly (Table 2). The experiment data matched reasonably well with the theoretical ones.

room temperature and filtered. The filtrates were evaporated and the crude product was purified by a silica gel column using hexane as eluent. 1,2-Bis(4-methoxyphenyl)-1,2-diphenylethene (TPE-OMe) was isolated in 91% yield. TPE-OMe is represented by the following chemical structure:

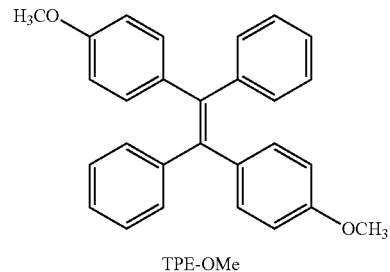 [SMILES: COc1ccc(/C(=C(\c2ccccc2)c2ccc(OC)cc2)c2ccccc2)cc1]

TPE-OMe

TPE-OMe (1.40 g, 3.56 mmol) was dissolved in 20 mL of dichloromethane (DCM) in a 100 mL flask, and the flask was placed in an acetone-dry ice bath at −78° C. A solution of 3.59 g (14.3 mmol) of boron tribromide in 10 mL of DCM

TABLE 2

| dTTP (μM) | 150 | 134 | 100 | 66 | 50 | 20 | 0 |
|---|---|---|---|---|---|---|---|
| SITC-dUTP (μM) | 50 | 66 | 100 | 134 | 150 | 180 | 200 |
| SITC-dUTP/(SITC-dUTP + dTTP) | 25% | 33% | 50% | 66% | 75% | 90% | 100% |
| Theoretic DOL (number of dyes/100 bases) | 5.34 | 7.04 | 10.68 | 14.10 | 16.02 | 19.22 | 21.36 |
| Experimental DOL (number of dyes/100 bases) | 5.31 ± 1.95 | 6.40 ± 1.61 | 7.41 ± 3.56 | 9.49 ± 2.48 | 17.96 ± 0.69 | 18.95 ± 7.07 | 21.56 ± 8.07 |
| DNA product concentration (mg/mL) | 29.49 ± 2.17 | 25.13 ± 6.39 | 23.17 ± 1.43 | 23.64 ± 1.89 | 19.46 ± 2.77 | 21.65 ± 3.18 | 16.88 ± 4.53 |

Figure 21:
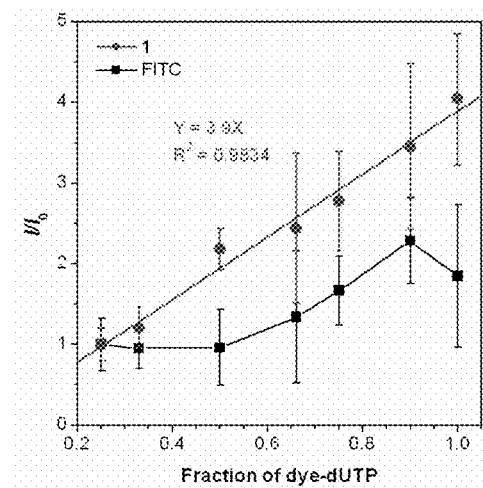
FIG. 21 illustrates the normalized fluorescence of labeled DNA versus the fraction of dye-dUTP.

To demonstrate the advantage of SITC labeled DNA over traditional dye label DNA on fluorescence quenching effect, FITC, a widely used traditional fluorescent dye, was selected to prepare the fluorescent DNA with the same PCR protocol as that used by SITC. The PL intensities of both FITC labeled DNA products and SITC labeled DNA products were measured at the same time. The PL peak intensities of the products prepared with the lowest fraction of dye-dUTP were used as the reference and plots of the normalized fluorescence versus the fraction of dye-dUTP were obtained (FIG. 21). The fluorescence intensity of SITC labeled DNA increased linearly with an increase in the fraction of dye-dUTP and reached the highest value when dTTP was completely replaced with SITC-dUTP. On the other hand, fluorescence quenching effect was observed for FITC labeled DNA when the fraction of dye-dUTP was over 0.9. The quenching effect would be even more obvious when T-rich templates are used. This inherent fluorescence quenching effect of the traditional fluorescent dye inhibits the complete substitution of normal dNTPs with dye modified ones and therefore the fluorescent DNA with high DOL could not be obtained.

Example 8

Preparation of TPE-OMe and TPE-OH

A suspension of p-methoxybenzophenone (1.06 g, 5.0 mmol), 1.34 equiv of TiCl$_4$/AlCl$_3$ (5.81 g, 6.7 mmol), and 25 equiv of Zn dust (8.01 g, 122.0 mmol) in 100 mL of dry THF was refluxed for 20 h. The reaction mixture was cooled to was added carefully to the mixture under stirring. The resultant mixture was allowed to warm to room temperature overnight under stirring. The reaction product was hydrolyzed by careful shaking with 20 mL of water. The organic phase was separated and concentrated by a rotary evaporator. The crude product was purified by recrystallization from THF/methanol to afford a white solid in 97% yield.

Characterization data of TPE-OMe: $^1$H NMR (CDCl$_3$, 300 MHz) δ (ppm): 7.10-7.06 (m, 10H), 6.93 (t, 4H), 6.64 (t, 4H), 3.74 (s, 6H). $^{13}$C NMR (CDCl$_3$, 75 MHz) δ (ppm): 158.0, 144.4, 139.7, 136.5, 132.6, 131.5, 127.8, 126.3, 113.2, 55.2. MS (TOF) m/e: 392.1 (M+, calcd. 392.2).

Characterization date of TPE-OH: $^1$H NMR (CDCl$_3$, 300 MHz) δ (ppm): 7.11-7.02 (m, 10H), 6.88 (t, 4H), 6.56 (d, 4H). $^{13}$C NMR (CDCl$_3$, 75 MHz) δ (ppm): 154.1, 144.2, 139.7, 135.5, 132.8, 131.5, 127.8, 126.3, 114.7. MS (TOF) m/e: 363.1 [(M-H)+, calcd: 363.1]. TPE-OH is represented by the following chemical formula:

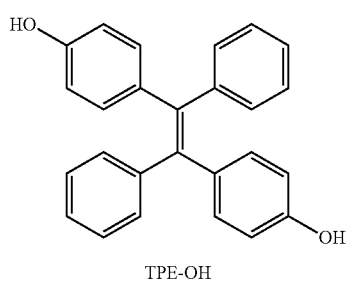 [SMILES: Oc1ccc(/C(=C(\c2ccccc2)c2ccc(O)cc2)c2ccccc2)cc1]

TPE-OH

Example 9

Preparation of TPE-SO3

TPE-OH (0.5 g, 1.37 mmol) and 20 mL of anhydrous ethanol were added into a 100 mL round-bottom flask under nitrogen. The mixture was stirred until all solids disappeared. A mixture of NaOEt (0.20 g, 3.0 mmol) in 20 mL ethanol was added dropwise and stirred for 1 h, causing the colorless solution to turn orange-red. 0.35 g of 1,3-propanesultone (2.88 mmol) in 20 mL of ethanol was added into the solution. The mixture was vigorously stirred for 12 h and a white product precipitated out from the solution. The product was collected by filtration and washed with ethanol and acetone twice to give a white solid in 61% yield.

Characterization data of TPE-SO3: $^1$H NMR (DMSO-d6, 300 MHz) δ (ppm): 7.25-7.13 (m, 6H), 7.08-7.02 (m, 4H), 6.95-6.90 (m, 4H), 6.81-6.73 (m, 4H), 4.09-4.02 (m, 4H), 2.66-2.58 (m, 4H), 2.08-2.02 (m, 4H). $^{13}$C NMR (DMSO-d6, 75 MHz) δ (ppm): 157.0, 143.9, 139.2, 135.5, 131.9, 130.8, 127.8, 126.2, 113.8, 66.4, 47.9, 25.3. MS (TOF) m/e: 631.1 [(M+2H)+–Na, calcd. 631.1], 609.2 [(M+3H)$^+$–2Na, calcd. 609.1].

Example 10

Fluorescence Labeling with TPE-SO3

To demonstrate the advantage of physically labeled proteins over traditional dye label proteins on fluorescence quenching effect, bovine serum albumin (BSA) was selected as model protein and dissolved in a phosphate buffer solution (5 μM) having a pH of 7.0. Fluorescence labeling was carried out by sequentially adding solutions of TPE-SO3 to 100 μL aliquots of BSA solutions. The mixtures were stirred for half an hour prior to taking their spectra.

Figure 22:
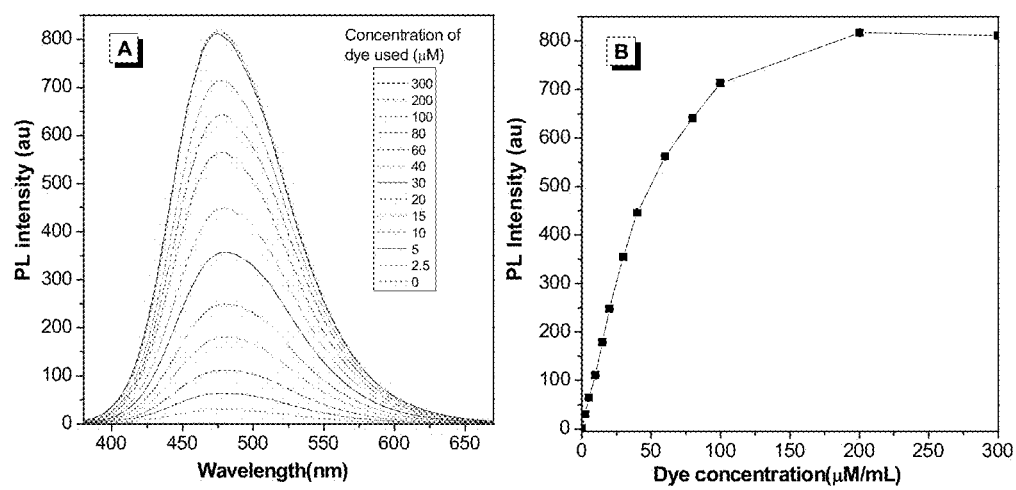
FIG. 22a illustrates the emission spectra of BSA (5 μM) labeled with different concentration of TPE-SO3. $\lambda_{ex}$=360 nm.
FIG. 22b illustrates the photoluminescence peak intensity of BSA (5 μM) labeled with different concentration of TPE-SO3. $\lambda_{em}$=475 nm.

The PL peak intensities of the BSA prepared with the lowest concentrations of TPE-SO3 were used as the reference and plots of the normalized fluorescence versus the concentrations of TPE-SO3 were obtained (FIG. 22). The fluorescence intensity of TPE-SO3 labeled BSA increased continuously with an increase in the concentrations of TPE-SO3. TPE-SO3 is represented by the following chemical formula:

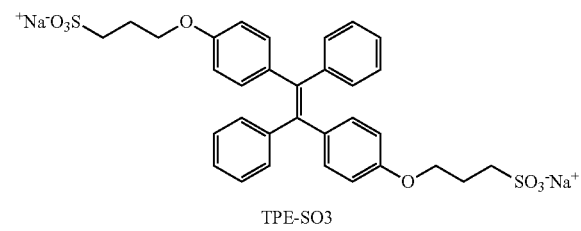

TPE-SO3

Example 11

Synthesis of TPEITC

THF, toluene, and dichloromethane were purified by simple distillation under nitrogen immediately prior to use. Carbon tetrachloride, DMSO, ether, carbon disulfide, diphenylmethane, 4-methylbenzophenone, 2.5 M solution of n-butyllithium in hexane, p-Toluenesulfonic acid (PTSA), N-bromosuccinimide (NBS), benzoyl peroxide (BPO), triphenylphosphine, sodium azide, acetic acid, chitosan, sodium hydroxide, hydrogen peroxide and other reagents were all purchased from Sigma and Aldrich and used as received. 1-(4-(azidomethyl)phenyl)-1,2,2-triphenylethylene (6) was prepared using previously reported procedures (See Yu, Y.; Liu, J.; Zhao, Z.; Ng, K. M.; Luo, K. Q.; Tang, B. Z. Chem. Commun. 2012, 48, 6360-6362).

$^1$H NMR and $^{13}$C NMR spectra were recorded on a Bruker ARX 400 spectrometer. HR mass spectra were recorded on a Finnigan TSQ 7000 triple quadrupole spectrometer operating in the MALDI-TOF mode. Fluorescence spectra were recorded on a Perkin-Elmer LS 50B spectrofluorometer with xenon discharge lamp excitation.

TPEITC fluorogens were synthesized according to Scheme 4.

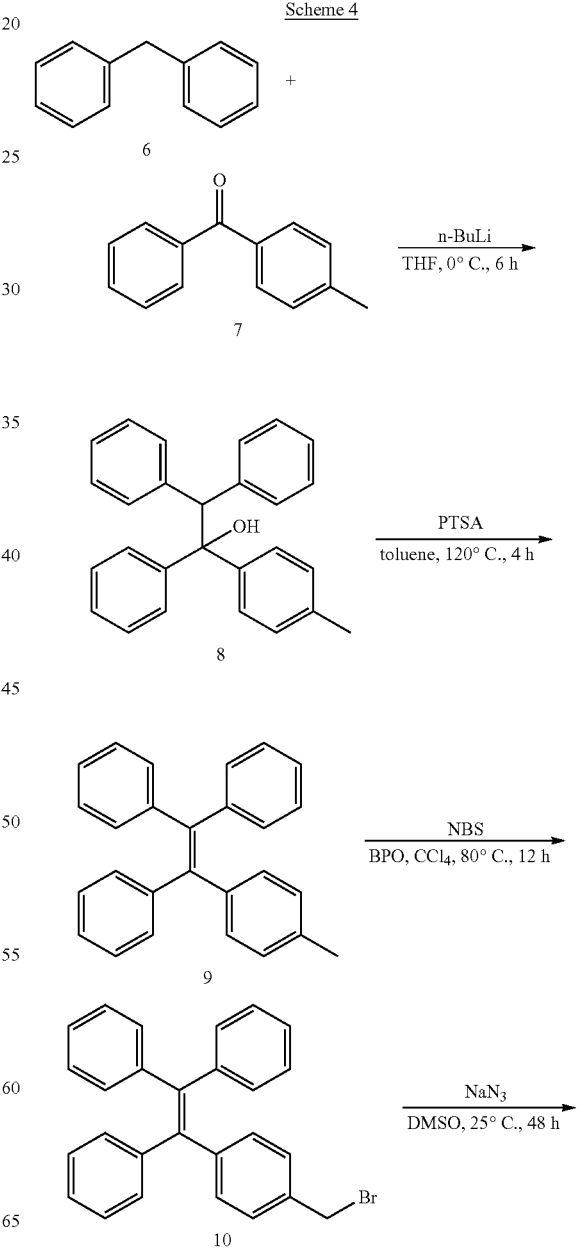

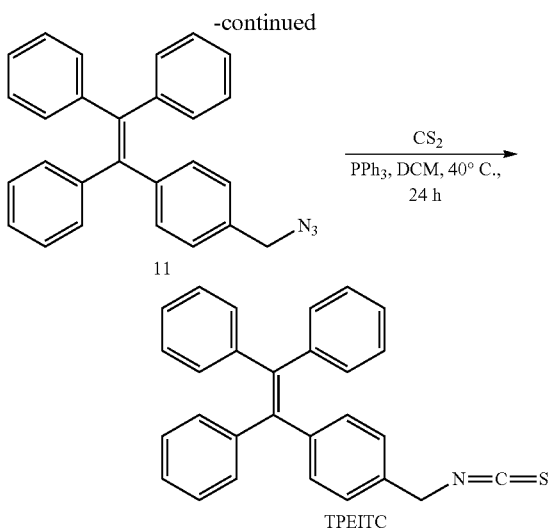

TPEITC

Compound 11 (Scheme 4, 0.33 g, 0.852 mmol), and triphenylphosphine (0.112 g, 0.426 mmol) were added into a two-necked flask, and then evacuated under vacuum and flushed with dry nitrogen three times. Carbon disulfide (0.55 g, 7.242 mmol) and distilled dichloromethane (50 mL) were added into flask under stirring. The resultant mixture was refluxed overnight, and then the solvent was removed under reduced pressure. The crude product was precipitated with cold ether (250 ml), then filtered and washed with cold ether (30 ml) three times. At last the product was dried under vacuum, and white solid was obtained in 85.2% yield.

Characterization Data of TPEITC (Scheme 4): $^1$H NMR (400 MHz, CDCl$_3$), δ (ppm): 7.00-7.13 (m, 19H), 4.63 (s, 2H). HRMS (MALDI-TOF), m/e: 403.1386 ([M]$^+$, calcd 403.1395).

Figure 23:
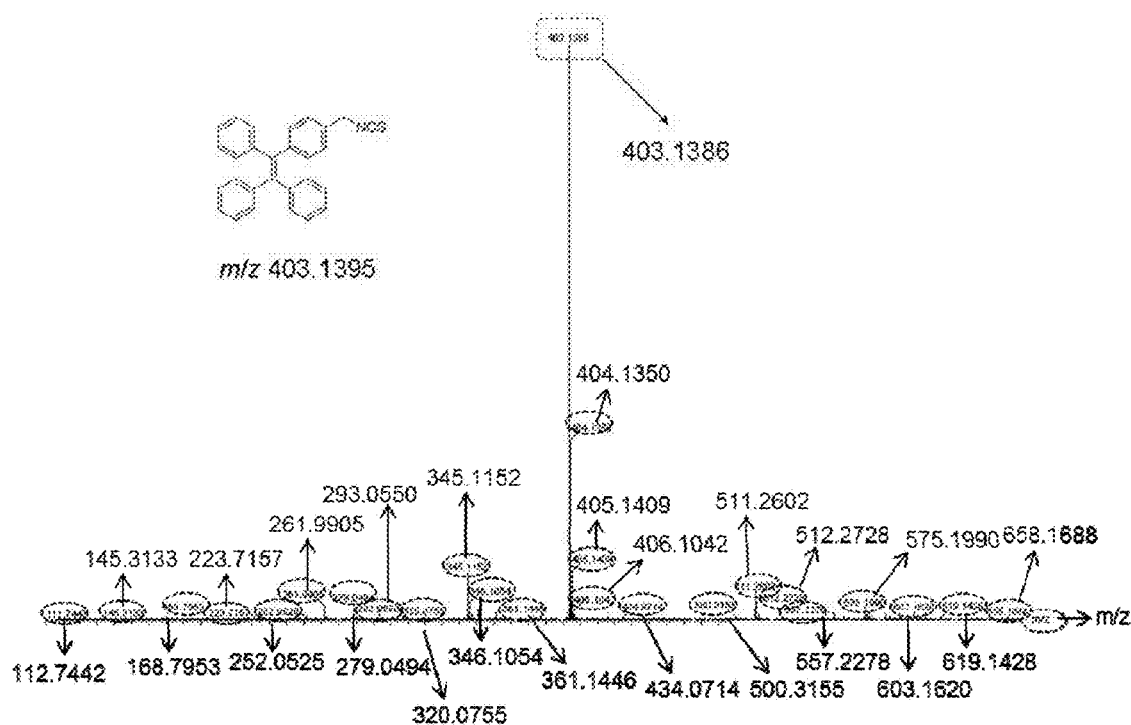
FIG. 23 shows a HRMS spectrum of TPEITC. HRMS (MALDI-TOF), m/e: 403.1386 ([M]$^+$, calcd 403.1395).
Figure 24:
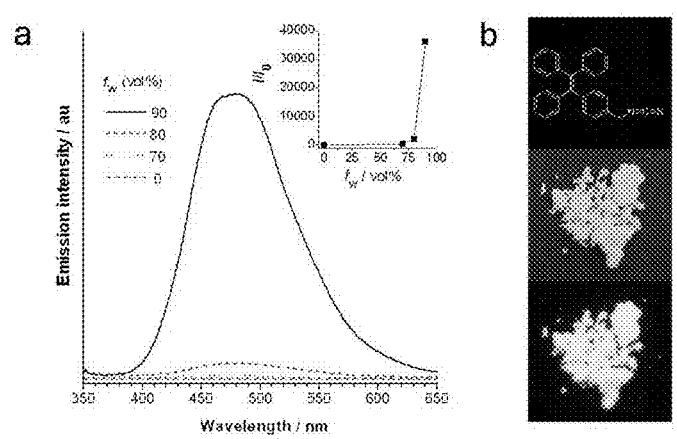
FIG. 24a shows the fluorescence spectra of TPEITC in THF/water mixtures with different fractions of water (4).
FIG. 24b shows the molecular structure and photographs of TPEITC solid powder taken under laboratory lighting (upper panel) and UV illumination (lower panel).
Figure 26:
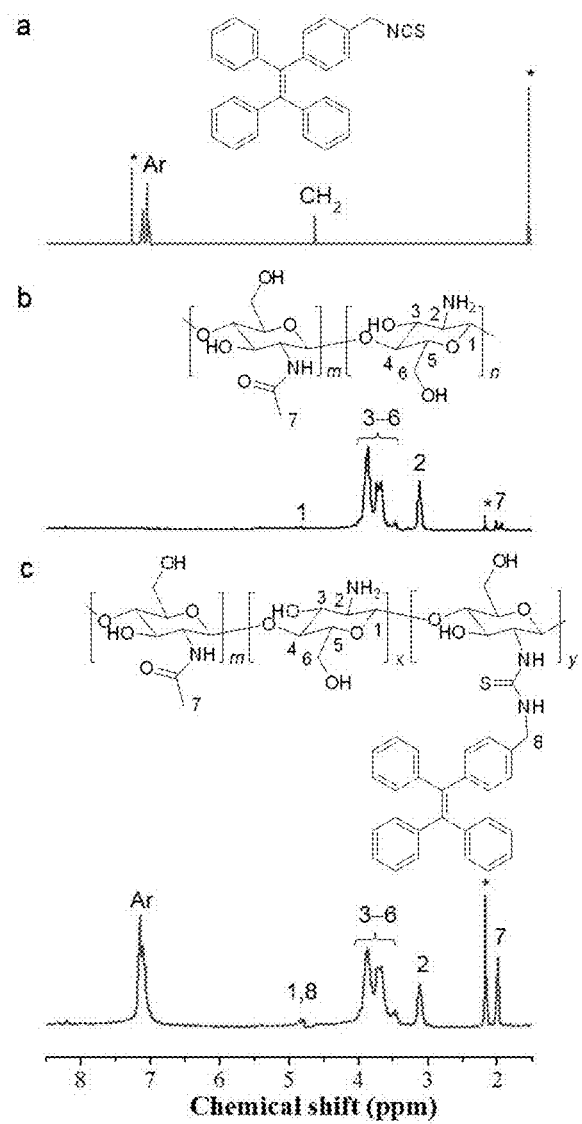
FIG. 26a shows the $^1$H NMR spectrum TPEITC in deuterated chloroform at room temperature. The solvent peaks are marked with asterisks.
FIG. 26b shows the $^1$H NMR spectrum of CS in deuterated acetic acid/water mixture at room temperature. The solvent peaks are marked with asterisks.
FIG. 26c shows the $^1$H NMR spectrum of TPEITC-CS in deuterated acetic acid/water mixture at room temperature. The solvent peaks are marked with asterisks.
Figure 27:
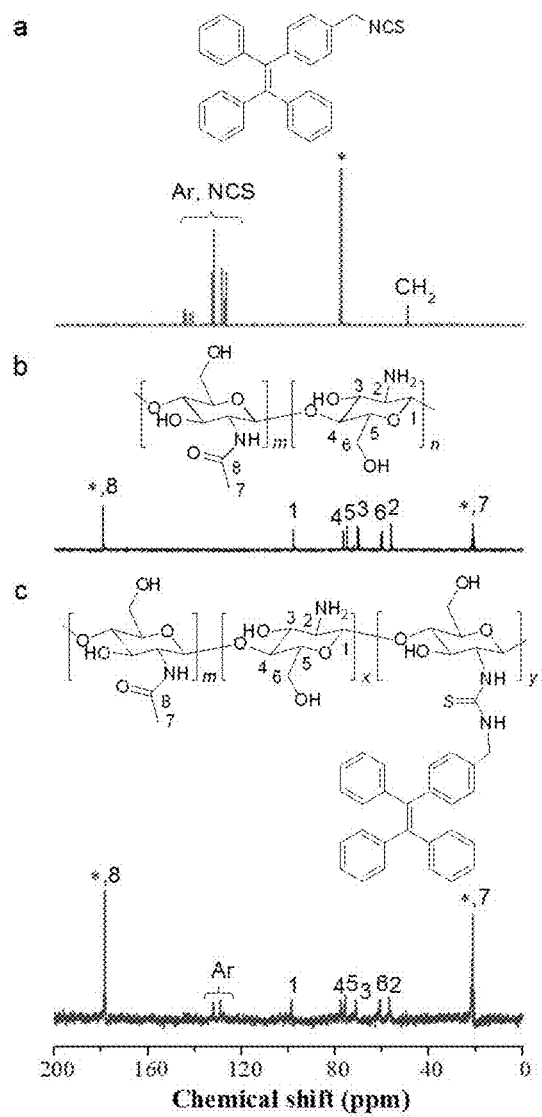
FIG. 27a shows the $^{13}$C NMR spectrum TPEITC in deuterated chloroform at room temperature. The solvent peaks are marked with asterisks.
FIG. 27b shows the $^{13}$C NMR spectrum of CS in deuterated acetic acid/water mixture at room temperature. The solvent peaks are marked with asterisks.
FIG. 27c shows the $^{13}$C NMR spectrum of TPEITC-CS in deuterated acetic acid/water mixture at room temperature. The solvent peaks are marked with asterisks.
Figure 28:
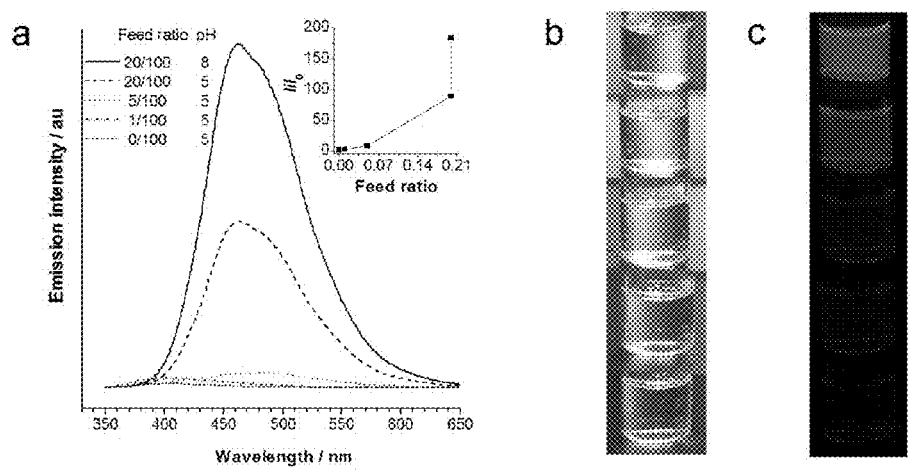
FIG. 28a shows the fluorescence spectra of TPEITC-CS in 0.1 M aqueous acetic acid solution prepared from different molar feed ratios. Concentration: 0.1 mg/mL. Inset: Plot of relative photoluminescence intensity (I/I$_0$) versus the molar feed ratio. I$_0$=photoluminescence intensity of chitosan in 0.1 M aqueous acetic acid solution. pH of the highest point is 8, others are 5.
FIG. 28b shows a photograph of solutions of TPEITC-CS prepared from different molar feed ratios in 0.1 M aqueous acetic acid solution taken under laboratory lighting.
FIG. 28c shows photograph of solutions of TPEITC-CS prepared from different molar feed ratios in 0.1 M aqueous acetic acid solution taken under UV illumination from a hand-held UV lamp.

Structure of dye is confirmed by standard spectroscopic methods (FIGS. 23, 26a, and 27a). In order to confirm TPEITC is AIE-active, we investigated its fluorescence in THF/water mixtures with different water fractions. As shown in FIG. 24a, almost no fluorescence signals are detected when TPEITC was dissolved in pure THF, because the multiple phenyl rings of dyes undergo active intramolecular rotations in the solution, which effectively annihilate their excited states and hence render them nonemissive. However, when large amounts of water (>80 vol %) are added into THF solution, TPEITC molecules become aggregated and fluorescence intensity dramatically increased. In the THF/water mixture with a water content of 90 vol %, the fluorescence intensity (I) became about 36177-fold stronger than that in the pure THF solution (I$_0$; FIG. 24a, inset). TPEITC molecules with hydrophobic aromatic cores precipitated and became aggregate in the nonsolvent mixture. Aggregation blocks the nonradiative relaxation channels and populates the radiative decay, thus resulting in high luminescence. Moreover, TPEITC powders become highly emissive in the solid state (FIG. 24b).

Example 12

Degradation of Chitosan

Chitosan (6 g) was added into distilled water (190 mL) and acetic acid (4 mL) mixture solution, stirred for 1 h and heated to 65° C. Then hydrogen peroxide (6 mL) was added into the chitosan solution, and stirred for 6 h. The degraded chitosan was precipitated with 10% sodium hydroxide solution, and filtered and washed with distilled water until it became neutral. The product was lyophilized at −50° C. for 72 h. The deacetylation degree of chitosan is 93.64%, which was determined by conductometric titration using a conductivity meter DDS-307 equipped with a Pt electrode for the measurement. Viscosity-average molecular weight of chitosan was 1.16×10$^6$, and decreased to 5.60×10$^4$ due to the degradation, which was measured by an Ubbelohde viscometer at 25±0.5° C. with 0.1 M HAc-0.2 M NaAc as solvent.

Example 13

Synthesis of TPEITC-CS

Chitosan macromolecules were labeled by TPEITC (marked with TPEITC-CS), its molecular structure is shown below.

The degraded chitosan (0.1 g, 0.621 mmol) was added into a two-necked flask, and then evacuated under vacuum and flushed with dry nitrogen three times. DMSO (10 mL) was added into flask, and stirred for 24 h at 60° C. Then a certain amount of TPEITC was added into flask so that the molar feed ratios of TPEITC/chitosan were equal to 1/100, 5/100 and 20/100. Then the solution was stirred for another 24 h. The product was washed with distilled water 5 times and acetone 3 times. And then the product was dissolved in an acetic acid aqueous solution. Equal volume of acetone was added. The product precipitated with 10% sodium hydroxide solution. Then, the product was filtered and washed with distilled water until it became neutral. TPEITC-CS was dried under vacuum at 60° C.

Figure 25:
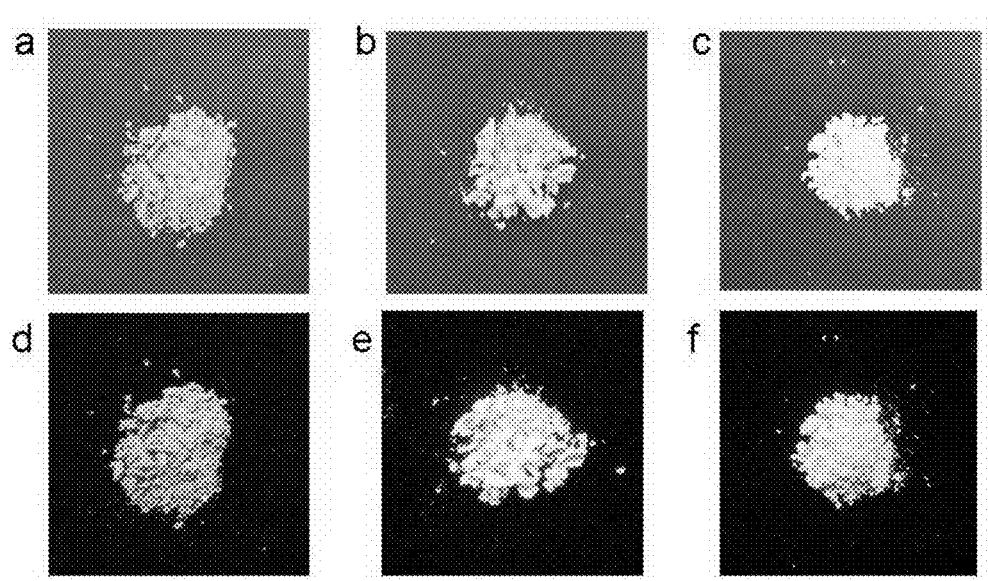
FIG. 25a shows a photograph of TPEITC-CS with the molar feed ratio of dye/CS (1/100), taking under daylight.
FIG. 25b shows a photograph of TPEITC-CS with the molar feed ratio of dye/CS (5/100), taking under daylight.
FIG. 25c shows a photograph of TPEITC-CS with the molar feed ratio of dye/CS (20/100), taking under daylight.
FIG. 25d shows a photograph of TPEITC-CS with the molar feed ratio of dye/CS (1/100), taking under UV illumination.
FIG. 25e shows a photograph of TPEITC-CS with the molar feed ratio of dye/CS (5/100), taking under UV illumination.
FIG. 25f shows a photograph of TPEITC-CS with the molar feed ratio of dye/CS (20/100), taking under UV illumination.

TPEITC-CS changed from light yellow to white under daylight when the molar feed ratios of dye/CS were increased (FIG. 25). When the labeled chitosan samples are excited under UV light, more TPEITC molecules labeled onto chitosan macromolecules. This enabled TPEITC-CS to emit much stronger fluorescence because the rotations of TPEITC luminogens are restricted, and block the nonradiative relaxation channel and populate the radiative decay. TPEITC-CS was labeled successfully, as confirmed by $^1$H NMR and $^{13}$C NMR spectra (FIGS. 26 and 27), which show proton and carbon chemical shifts of benzene rings in TPEITC-CS deuterated acetic acid/water solution. Labeling efficiencies of TPEITC-CS were calculated by UV and NMR spectroscopies, the results of which are shown in Table 3, below. TPEITC is easier for chitosan labeling because there is one methylene group between benzene ring and isothiocyanate group (—N═C═S) in TPEITC molecule that results in elimination of conjugative effect and lower hindering effect.

TABLE 3

Labeling efficiencies of TPEITC-CS[a].

| Feed ratio[b] | UV | NMR |
|---|---|---|
| 1/100 | 0.88/100 | 0.83/100 |
| 5/100 | 2.76/100 | 2.77/100 |
| 20/100 | 7.20/100 | 7.86/100 |

[a]Determined by UV and NMR spectroscopies.
[b]Feed ratio = dye/CS.

Example 14

Cell Imaging

HeLa cells were grown overnight on a cover slid in a 35 mm Petri dish. The living cells were stained with TPEITC-CS (100 µg/mL) and incubated for 4 h, and the images were taken under a fluorescence microscope (Olympus BX41); excitation=330-380 nm, dichroic mirror=400 nm, longpass emission filter.

Figure 29:
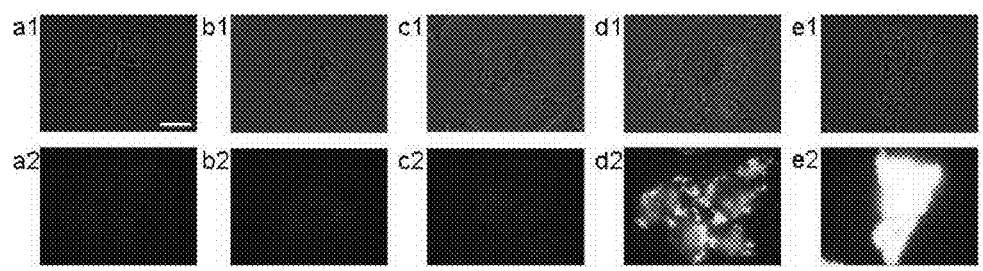
Figure 30:
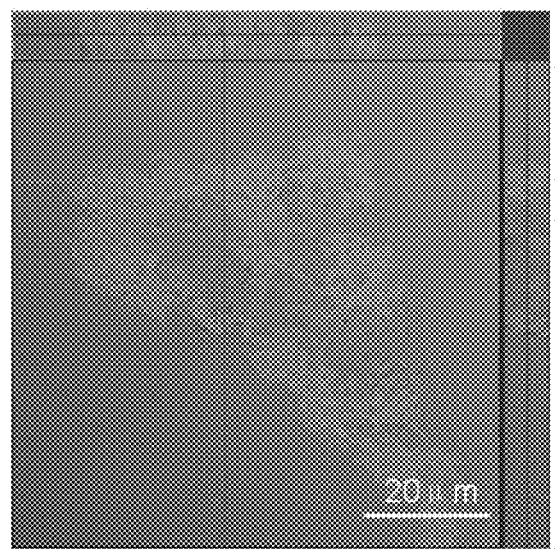
FIG. 30 shows an image (x, y-axis) captured by confocal laser scanning microscope (CLSM), with respective projections of the x, z-, and y, z-axes, of HeLa cells incubated with 0.1 mg/mL TPEITC-CS (20/100) solution.

TPEITC-CS was used for intracellular imaging. HeLa cells were imaged by chitosan and TPEITC-CS solution using a standard cell-staining protocol. The results are shown in FIG. 29, nearly no fluorescence signal was detected when the HeLa cells were cultured in the absence of chitosan and the presence of TPEITC-CS (1/100). As the feed ratio of TPEITC/CS increased to 5/100, the cells were stained and became emissive. Surprisingly, very strong emission was recorded when the HeLa cells were stained by TPEITC-CS (20/100), although the exposure time was as short as 0.5 s, indicating that it is very sensitive for cell imaging. A three-dimensional analysis was conducted by confocal laser scanning microscope (CLSM) (FIG. 30). In particular the reconstruction of the z-axis, indicating that fluorescent signals are located within the cells stained by TPEITC-CS.

Example 15

Co-Culture of HeLa and 3T3 Cells

HeLa cells were stained with TPEITC-CS solution (100 µg/mL) for 4 h. After washing five times with PBS, the stained HeLa cells and unstained 3T3 cells were detached from their respective culture dishes by treating with trypsin-EDTA solution. $1.5 \times 10^3$ stained HeLa cells and $2.5 \times 10^3$ unstained 3T3 cells were re-suspended with 2 mL of DMEM and transferred into a new 25-mm Petri dish. After 12 h incubation at 37° C., both phase contrast and fluorescence images of the co-cultured cells were obtained from the same region. The images were taken under a Zeiss laser scanning confocal microscope (model: LSM7 DUO). Excitation: 405 nm, filter: 449-520 nm.

Figure 31:
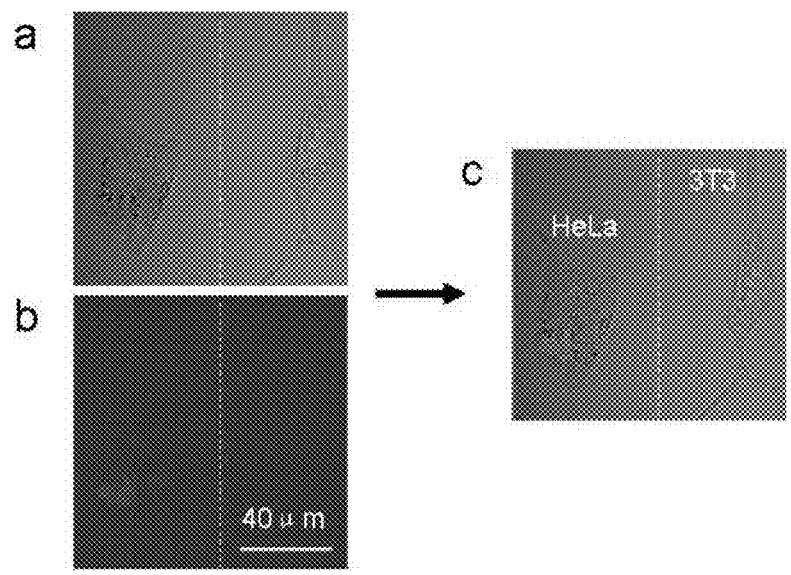
FIG. 31a shows a bright-field image of the TPEITC-CS-stained HeLa cells co-cultured with unstained 3T3 cells captured by CLSM.
FIG. 31b shows a fluorescent image of the TPEITC-CS-stained HeLa cells co-cultured with unstained 3T3 cells captured by CLSM.
FIG. 31c shows an overlapping image of the TPEITC-CS-stained HeLa cells co-cultured with unstained 3T3 cells captured by CLSM.

Leakage of TPEITC-CS was examined by cell co-culture method. Few traditional dyes can be retained in live cells for more than a couple of hours under physiological conditions due to the dyes are leaking to extracellular media. To examine whether TPEITC-CS will diffuse from intracellular to extracellular media or not, TPEITC-CS-stained HeLa cells were co-cultured with unstained 3T3 cells because the two cell lines are very easy to be distinguished through their discernable morphologies. As can be seen from FIG. 31, HeLa cells are readily stained by TPEITC-CS, and dyes remained in HeLa cells without penetrating into 3T3 cells after they were co-cultured in a petri dish overnight. This indicated that TPEITC-CS was firmly retained inside the HeLa cells. During the imaging process, TPEITC-CS macromolecules were enclosed by the cell membrane to form small vesicles that can be internalized by the cell. Inside the cell, macromolecular dyes can be further processed in endosomes and lysosomes and are eventually released from the cellular organelles. When TPEITC-CS macromolecules were bound to the biomacromolecules in the cytoplasm, they became more emissive, due to the additional physical restriction to the rotations of fluorogens.

Example 16

Long-Term Cell Tracing $3 \times 10^5$ HeLa cells were cultured overnight and stained on a Petri dish at 50% confluence by TPEITC-CS solution (100 µg/mL). After taking an image at the end of 24 h of incubation, referred to as the end of the 1st passage, 25% of the cells in the completely filled Petri dish were transferred to a new dish with a fresh growth medium. Another image was taken after 24 h in the then half-filled Petri dish, i.e., the end of the 2nd passage. The cells were further incubated for another 24 h, i.e., to the end of the 3rd passage. The processes were repeated to proceed to the 16th passage until no fluorescent cells could be observed.

Figure 32:
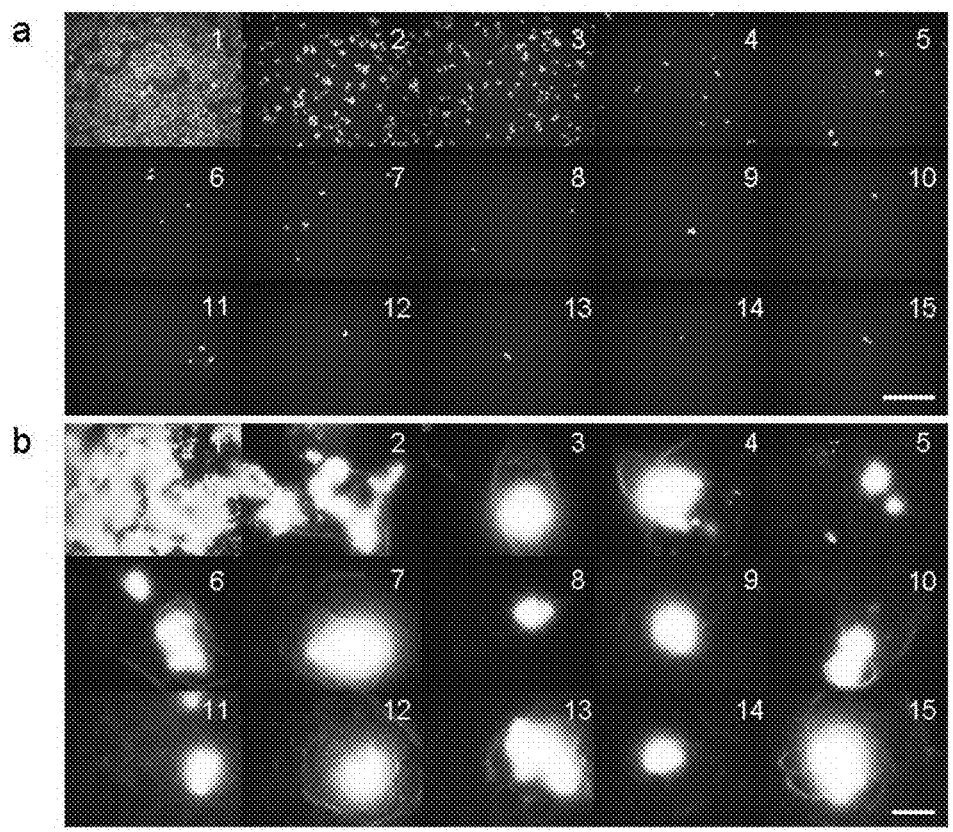
FIG. 32a shows fluorescent images of the TPEITC-CS-stained HeLa cells at different passages over 15 days, and magnified by 100 times; bar: 30 μm.
FIG. 32b shows fluorescent images of the TPEITC-CS-stained HeLa cells at different passages over 15 days, and magnified by 1000 times; bar: 30 μm.

TPEITC-CS was used for long-term cell tracing. TPEITC-CS with AIE fluorogen cores is highly emissive, and has strong binding ability to the cell cytoplasmic region, suggesting that it may be used for long-term cell tracing. As can be seen from FIG. 32, bright HeLa cells stained by TPEITC-CS could still be detected after 15 passages. Almost no FL signals were detectable in the MitoTracker Green FM (MTG)-stained cells after only two passages, due to its low working concentration and fast leakage. However, TPEITC-CS could trace the live cells for a long-term because TPEITC-CS macromolecular chains were firmly retained inside the HeLa cells. This enables the novel CS-based cytophilic bioprobes with AIE characteristics to be used for tracing invasion, diffusion, and spread as well as suppression, shrinkage, and necrosis processes of cancer cells.

With the information contained herein, various departures from precise descriptions of the present subject matter will be readily apparent to those skilled in the art to which the present subject matter pertains, without departing from the spirit and the scope of the below claims. The present subject matter is not considered limited in scope to the procedures, properties, or components defined, since the preferred embodiments and other descriptions are intended only to be illustrative of particular aspects of the presently provided subject matter. Indeed, various modifications of the described modes for carrying out the present subject matter which are obvious to those skilled in chemistry, biochemistry, or related fields are intended to be within the scope of the following claims.

The invention claimed is:

1. A method of preparing a fluorescent bioprobe comprising the following steps:

(i) synthesizing fluorogens with one or more amine- or thiol-reactive functional groups; and (ii) labeling a biomolecule with the fluorogens via a reaction between the fluorogens and one or more amine or thiol groups of the biomolecule;

wherein the one or more amine- or thiol-reactive functional groups are selected from the group consisting of isocyanates, isothiocyanates, aldehydes, succinimidyl esters, 4-sulfotetrafluorophenyl esters, 2,4,5,6-tetrafluorophenyl esters, sulfodicholorphenol esters, carbonyl azides, sulfonyl chlorides, and haloacetamides;

wherein the fluorescent bioprobe emits fluorescence;

wherein the fluorogens exhibit aggregation-induced emission and comprise a backbone structure selected from the group consisting of:

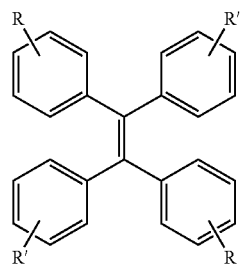

and

-continued

[structure: silole with four phenyl groups and R, R' substituents]

wherein:
each R and R' are independently selected from the group consisting of: H, $C_nH_{2n+1}$, $OC_nH_{2n+1}$, $C_6H_5$, $OC_6H_5$, and $(X)_nN[(CH_2)_mCH_3]_2$;
X is selected from the group consisting of $(CH_2)_n$, $C_6H_5$, and $O(CH_2)_n$; and
n, m independently=an integer from 0 to 20; and
wherein the biomolecule is one or more selected from the group consisting of a nucleotide, nucleoside, oligonucleotide, and DNA, each comprising a reactive thiol or amine group, proteins, and chitosan.

2. The method of claim 1, wherein the labeling is carried out without a fixation process.

3. The method of claim 1, wherein the labeling step is carried out without self-quenching.

4. A method of in vitro cell imaging comprising:
(a) contacting cells with a fluorescent bioprobe; and
(b) detecting cellular fluorescence via fluorescent microscopy,
wherein the fluorescent bioprobe comprises a biomolecule covalently conjugated with one or more fluorogens;
wherein the fluorescent bioprobe emits fluorescence;
wherein the one or more fluorogens exhibit aggregation-induced emission and comprise a backbone structure selected from the group consisting of:

[tetraphenylethylene structure with R, R' substituents]

and

[silole structure with phenyl groups and R, R' substituents]

wherein:
each R and R' are independently selected from the group consisting of: H, $C_nH_{2n+1}$, $OC_nH_{2n+1}$, $C_6H_5$, $OC_6H_5$, and $(X)_nN[(CH_2)_mCH_3]_2$;
X is selected from the group consisting of $(CH_2)_n$, $C_6H_5$, and $O(CH_2)_n$; and
n, m independently=an integer from 0 to 20; and
wherein the biomolecule is selected from the group consisting of nucleosides, nucleotides, and oligonucleotides.

5. The method of claim 4, wherein the fluorescent microscopy is used for live cell tracking.

6. The method of claim 4, wherein the cells uptake the fluorescent bioprobe.

7. The method of claim 6, wherein the one or more fluorogens interact with the biomolecule inside cells via electrostatic attraction, hydrogen bonding, or hydrophobic interaction.

8. A method of in vitro cellular imaging comprising:
contacting target cells with a fluorescent bioprobe comprising luminogen formed nanoparticles for cellular imaging and long term cellular tracking comprising one or more luminogens that exhibit aggregation-induced emission properties;
wherein the luminogen formed nanoparticles are fully retained inside living cells and have a fluorescence emission;
wherein the one or more luminogens are represented by the structure:

[tetraphenylethylene structure with R, R' substituents]

wherein
each R and R' are independently selected from the group consisting of: H, $C_nH_{2n+1}$, $OC_nH_{2n+1}$, $C_6H_5$, $OC_6H_5$, and $(X)_nN[(CH_2)_mCH_3]_2$;
X is selected from the group consisting of $(CH_2)_n$, $C_6H_5$, and $O(CH_2)_n$; and
n, m independently=an integer from 0 to 20;
and detecting cellular fluorescence.

9. A method of in vitro cell imaging comprising:
(a) contacting cells with a fluorescent bioprobe; and
(b) detecting cellular fluorescence via fluorescent microscopy,
wherein the fluorescent bioprobe comprises a biomolecule covalently conjugated with one or more fluorogens;
wherein the fluorescent bioprobe emits fluorescence; and
wherein the one or more fluorogens exhibit aggregation-induced emission and are represented by the structure:

[chitosan-based structure conjugated with tetraphenylethylene via thiourea linkage]

* * * * *

SEQUENCE LISTING

<160> NUMBER OF SEQ ID NOS: 13

<210> SEQ ID NO 1
<211> LENGTH: 1061
<212> TYPE: DNA
<213> ORGANISM: Artificial Sequence
<220> FEATURE:
<223> OTHER INFORMATION: PCR product of plasmid DNA

<400> SEQUENCE: 1

| | | | | | |
|---|---|---|---|---|---|
| gggcccctgc | aggctaagct | aagttaactg | agctctactc | gagaacaagg | acgtcaacag | 60 |
| cttcgacttg | gacgaacaag | atttcgctga | cattgccaag | ttggacatca | acttgagatt | 120 |
| caacgaccca | tgggactggg | acaagattcc | tatcttcgtc | taaaagcttg | cgaatttctt | 180 |
| atgatttatg | atttttatta | ttaaataagt | tataaaaaaa | ataagtgtat | acaaatttta | 240 |
| aagtgactct | taggttttaa | aacgaaaatt | cttattcttg | agtaactctt | tcctgtaggt | 300 |
| caggttgctt | tctcaggtat | agcatgaggt | cgctcttatt | gaccacacct | ctaccggcat | 360 |
| gccgagcaaa | tgcctgcaaa | tcgctcccca | tttcacccaa | ttgtagatat | gctaactcca | 420 |
| gcaatgagtt | gatgaatctc | ggtgtgtatt | ttatgtcctc | agaggacaac | acctgttgta | 480 |
| atcgttcttc | cacacctcga | cgcttttcaa | ttcatctttt | tttttttttgt | tctttttttt | 540 |
| gattccggtt | tctttgaaat | ttttttgatt | cggtaatctc | cgagcagaag | gaagaacgaa | 600 |
| ggaaggagca | cagacttaga | ttggtatata | tacgcatatg | tggtgttgaa | gaaacatgaa | 660 |
| attgcccagt | attcttaacc | caactgcaca | gaacaaaaac | atgcaggaaa | cgaagataaa | 720 |
| tcatgtcgaa | agctacatat | aaggaacgtg | ctgctactca | tcctagtcct | gttgctgcca | 780 |
| agctatttaa | tatcatgcac | gaaaagcaaa | caaacttgtg | tgcttcattg | gatgttcgta | 840 |
| ccaccaagga | attactggag | ttagttgaag | cattaggtcc | caaaatttgt | ttactaaaaa | 900 |
| cacatgtgga | tatcttgact | gattttttcca | tggagggcac | agttaagccg | ctaaaggcat | 960 |
| tatccgccaa | gtacaatttt | ttactcttcg | aagacagaaa | atttgctgac | attggtaata | 1020 |
| cagtcaaatt | gcagtactct | gcgactagtg | aattcgggcc | c | | 1061 |

<210> SEQ ID NO 2
<211> LENGTH: 94
<212> TYPE: DNA
<213> ORGANISM: Artificial Sequence
<220> FEATURE:
<223> OTHER INFORMATION: DNA template

<400> SEQUENCE: 2

| | | | | | |
|---|---|---|---|---|---|
| tcgagaacaa | ggacgtcaac | agcttcgact | tggacgaaca | agatttcgct | gacattgcca | 60 |
| agttggacat | caacttgaga | ttcaacgacc | catg | | | 94 |

<210> SEQ ID NO 3
<211> LENGTH: 21
<212> TYPE: DNA
<213> ORGANISM: Artificial Sequence
<220> FEATURE:
<223> OTHER INFORMATION: DNA Primer

<400> SEQUENCE: 3
tcgagaacaa ggacgtcaac a                                          21

<210> SEQ ID NO 4
<211> LENGTH: 204
<212> TYPE: DNA
<213> ORGANISM: Artificial Sequence
<220> FEATURE:
<223> OTHER INFORMATION: DNA template

<400> SEQUENCE: 4
cacagaacaa aaacatgcag gaaacgaaga taaatcatgt cgaaagctac atataaggaa    60
cgtgctgcta ctcatcctag tcctgttgct gccaagctat ttaatatcat gcacgaaaag   120
caaacaaact tgtgtgcttc attggatgtt cgtaccacca aggaattact ggagttagtt   180
gaagcattag gtcccaaaat ttgt                                          204

<210> SEQ ID NO 5
<211> LENGTH: 21
<212> TYPE: DNA
<213> ORGANISM: Artificial Sequence
<220> FEATURE:
<223> OTHER INFORMATION: DNA primer

<400> SEQUENCE: 5
cacagaacaa aaacatgcag g                                              21

<210> SEQ ID NO 6
<211> LENGTH: 304
<212> TYPE: DNA
<213> ORGANISM: Artificial Sequence
<220> FEATURE:
<223> OTHER INFORMATION: DNA template

<400> SEQUENCE: 6
tcgagaacaa ggacgtcaac agcttcgact tggacgaaca agatttcgct gacattgcca    60
agttggacat caacttgaga ttcaacgacc catgggactg ggacaagatt cctatcttcg   120
tctaaaagct tgcgaatttc ttatgattta tgatttttat tattaaataa gttataaaaa   180
aaataagtgt atacaaattt taaagtgact cttaggtttt aaaacgaaaa ttcttattct   240
tgagtaactc tttcctgtag gtcaggttgc tttctcaggt atagcatgag gtcgctctta   300
ttga                                                                304

<210> SEQ ID NO 7
<211> LENGTH: 21
<212> TYPE: DNA
<213> ORGANISM: Artificial Sequence
<220> FEATURE:
<223> OTHER INFORMATION: DNA primer

<400> SEQUENCE: 7
tcgagaacaa ggacgtcaac a                                              21

<210> SEQ ID NO 8
<211> LENGTH: 94
<212> TYPE: DNA
<213> ORGANISM: Artificial Sequence
<220> FEATURE:
<223> OTHER INFORMATION: DNA template

<400> SEQUENCE: 8
cacagaacaa aaacatgcag gaaacgaaga taaatcatgt cgaaagctac atataaggaa    60
cgtgctgcta ctcatcctag tcctgttgct gcca                                94

<210> SEQ ID NO 9
<211> LENGTH: 21
<212> TYPE: DNA
<213> ORGANISM: Artificial Sequence
<220> FEATURE:

```
<223> OTHER INFORMATION: DNA primer

<400> SEQUENCE: 9
cacagaacaa aaacatgcag g                                         21

<210> SEQ ID NO 10
<211> LENGTH: 103
<212> TYPE: DNA
<213> ORGANISM: Artificial Sequence
<220> FEATURE:
<223> OTHER INFORMATION: DNA template

<400> SEQUENCE: 10
gttaagccgc taaaggcatt atccgccaag tacaattttt tactcttcga agacagaaaa    60
tttgctgaca ttggtaatac agtcaaattg cagtactctg cga                     103

<210> SEQ ID NO 11
<211> LENGTH: 20
<212> TYPE: DNA
<213> ORGANISM: Artificial Sequence
<220> FEATURE:
<223> OTHER INFORMATION: DNA primer

<400> SEQUENCE: 11
gttaagccgc taaaggcatt                                           20

<210> SEQ ID NO 12
<211> LENGTH: 103
<212> TYPE: DNA
<213> ORGANISM: Artificial Sequence
<220> FEATURE:
<223> OTHER INFORMATION: DNA template

<400> SEQUENCE: 12
caggaaacag ctatgaccat gattacgaat tcgagctcgg tacccgggga tcctctagag    60
tcgacctgca ggcatgcaag cttggcactg gccgtcgttt tac                     103

<210> SEQ ID NO 13
<211> LENGTH: 17
<212> TYPE: DNA
<213> ORGANISM: Artificial Sequence
<220> FEATURE:
<223> OTHER INFORMATION: DNA primer

<400> SEQUENCE: 13
caggaaacag ctatgac                                              17
```